United States Patent
Iwaki et al.

(10) Patent No.: US 8,642,635 B2
(45) Date of Patent: *Feb. 4, 2014

(54) SUBSTITUTED CARBAMOYLMETHYLAMINO ACETIC ACID DERIVATIVES AS NOVEL NEP INHIBITORS

(71) Applicants: Yuki Iwaki, Cambridge, MA (US); Toshio Kawanami, Boston, MA (US); Gary Michael Ksander, Amherst, NH (US); Muneto Mogi, Waltham, MA (US)

(72) Inventors: Yuki Iwaki, Cambridge, MA (US); Toshio Kawanami, Boston, MA (US); Gary Michael Ksander, Amherst, NH (US); Muneto Mogi, Waltham, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,475

(22) Filed: Dec. 5, 2012

(65) Prior Publication Data
US 2013/0096168 A1  Apr. 18, 2013

Related U.S. Application Data

(62) Division of application No. 13/449,357, filed on Apr. 18, 2012, now Pat. No. 8,377,978, and a division of application No. 12/947,029, filed on Nov. 16, 2010, now Pat. No. 8,222,286.

(60) Provisional application No. 61/359,914, filed on Jun. 30, 2010, provisional application No. 61/263,137, filed on Nov. 20, 2009.

(51) Int. Cl.
*A61K 31/41* (2006.01)
*A61K 31/185* (2006.01)
*C07D 249/04* (2006.01)
*C07D 257/04* (2006.01)

(52) U.S. Cl.
USPC ........... 514/381; 514/553; 514/557; 514/579; 548/250; 562/400; 562/621

(58) Field of Classification Search
USPC ................. 514/381, 553, 557, 579; 548/250; 562/400, 621
See application file for complete search history.

(56) References Cited

U.S. PATENT DOCUMENTS

| | | |
|---|---|---|
| 4,281,180 A | 7/1981 | Umezawa et al. |
| 4,610,816 A | 9/1986 | Berger |
| 4,719,231 A | 1/1988 | Umezawa et al. |
| 4,721,726 A | 1/1988 | Berger |
| 4,738,803 A | 4/1988 | Roques et al. |
| 5,200,426 A | 4/1993 | Hersh et al. |
| 5,217,996 A | 6/1993 | Ksander |
| 5,250,522 A | 10/1993 | De Lombaert |
| 5,273,990 A | 12/1993 | De Lombaert |
| 5,294,632 A | 3/1994 | Erion et al. |
| 5,414,017 A | 5/1995 | Delaney et al. |
| 5,449,662 A | 9/1995 | Scarborough |
| 5,517,996 A | 5/1996 | Okada et al. |
| 5,550,119 A | 8/1996 | De Lombaert et al. |
| 5,710,171 A | 1/1998 | Dinsmore et al. |
| 5,891,912 A | 4/1999 | Kawashima et al. |
| 5,968,980 A | 10/1999 | Kawashima et al. |
| 6,169,103 B1 | 1/2001 | Purchase, Jr. et al. |
| 8,222,286 B2 * | 7/2012 | Iwaki et al. ................ 514/381 |
| 8,377,978 B2 * | 2/2013 | Iwaki et al. ................ 514/381 |
| 2002/0193562 A1 | 12/2002 | Robl |
| 2004/0063761 A1 | 4/2004 | Kuduk et al. |
| 2008/0119557 A1 | 5/2008 | Webb et al. |
| 2008/0188533 A1 | 8/2008 | Choi et al. |
| 2008/0269305 A1 | 10/2008 | Allegretti et al. |
| 2010/0305131 A1 | 12/2010 | Coppola et al. |
| 2010/0305145 A1 | 12/2010 | Coppola et al. |
| 2012/0202862 A1 * | 8/2012 | Iwaki et al. ................ 514/380 |

FOREIGN PATENT DOCUMENTS

| | | |
|---|---|---|
| EP | 0038046 A2 | 10/1981 |
| EP | 0077274 A1 | 4/1983 |
| EP | 0082088 A1 | 6/1983 |

(Continued)

OTHER PUBLICATIONS

Bhagwat et al.; "Alpha-Mercaptoacyl Dipeptides That Inhibit Angiotensin Converting Enzyme and Neutral Endopeptidase 24.11."; Bioorganic & Medicinal Chemistry Letters; 5(7):735-738 (1995).

De Lombaert et al.; "N-Phosphononnethyl Dipeptides and Their Phosphonate Prodrugs, a New Generation of Neutral Endopeptidase (NEP, EC 3.4.24.11) Inhibitors1"; J. Med. Chem.; 37(4):498-511 (1994).

De Lombaert et al.; "Chemical and Plasma Hydrolyses of a Diphenyl Alpha-Aminomethyl Phosphonate Prodrug Inhibitor of Neutral Endopeptidase 24.11"; Bioorganic & Med. Chem. Ltrs.; 4(7):899-902 (1994).

(Continued)

*Primary Examiner* — Susannah Chung
(74) *Attorney, Agent, or Firm* — Sophie Binet Cross

(57) ABSTRACT

The present invention provides a compound of formula I;

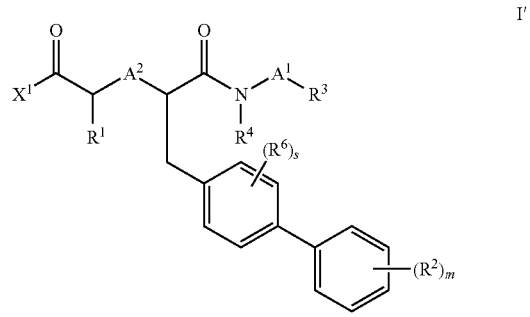

or a pharmaceutically acceptable salt thereof, wherein $R^1$, $R^2$, $R^3$, $R^4$, $R^6$, $A^1$, $A^2$, $X^1$, s and m are defined herein. The invention also relates to a method for manufacturing the compounds of the invention, and its therapeutic uses. The present invention further provides a combination of pharmacologically active agents and a pharmaceutical composition.

11 Claims, No Drawings

(56) References Cited

FOREIGN PATENT DOCUMENTS

| | | |
|---|---|---|
| EP | 0103077 A2 | 3/1984 |
| EP | 0117429 A1 | 9/1984 |
| EP | 0136883 A2 | 4/1985 |
| EP | 0262053 A2 | 3/1988 |
| EP | 0356124 A2 | 2/1990 |
| EP | 0497192 A2 | 8/1992 |
| EP | 0533130 A1 | 3/1993 |
| EP | 0534492 A2 | 3/1993 |
| EP | 1903027 A1 | 3/2008 |
| EP | 2 070 928 A1 | 6/2009 |
| FR | 2597865 A1 | 10/1987 |
| GB | 2037754 A | 7/1980 |
| GB | 2207351 A | 2/1989 |
| GB | 2354440 A | 3/2001 |
| JP | 4149166 A | 5/1992 |
| JP | 5262709 A | 10/1993 |
| JP | 6234630 A | 8/1994 |
| JP | 7157459 A | 6/1995 |
| JP | 2000344614 A | 12/2000 |
| JP | 2003321358 A | 11/2003 |
| WO | 9102718 A1 | 3/1991 |
| WO | 9109840 A1 | 7/1991 |
| WO | 9420457 A1 | 9/1994 |
| WO | 9535307 A1 | 12/1995 |
| WO | 9747270 A3 | 12/1997 |
| WO | 9809940 A1 | 3/1998 |
| WO | 9818803 A1 | 5/1998 |
| WO | 9853817 A1 | 12/1998 |
| WO | 9926921 A1 | 6/1999 |
| WO | 9926922 A1 | 6/1999 |
| WO | 9926923 A1 | 6/1999 |
| WO | 9936393 A1 | 7/1999 |
| WO | 0226696 A1 | 4/2002 |
| WO | 03059345 A1 | 7/2003 |
| WO | 2004062553 A2 | 7/2004 |
| WO | 2004099171 A2 | 11/2004 |
| WO | 2005012270 A2 | 2/2005 |
| WO | 2005014534 A1 | 2/2005 |
| WO | 2006020358 A2 | 2/2006 |
| WO | 2006055725 A2 | 5/2006 |
| WO | 2006069096 A1 | 6/2006 |
| WO | 2006086456 A2 | 8/2006 |
| WO | 2007045663 A2 | 4/2007 |
| WO | 2007056324 A2 | 5/2007 |
| WO | 2007056546 A1 | 5/2007 |
| WO | 2008031567 A1 | 3/2008 |
| WO | 2008073138 A2 | 6/2008 |
| WO | 2008083967 A2 | 7/2008 |
| WO | 2008138561 A1 | 11/2008 |
| WO | 2008153857 A1 | 12/2008 |
| WO | 2009061713 A1 | 5/2009 |
| WO | 2009076288 A1 | 6/2009 |
| WO | 2009090251 A2 | 7/2009 |
| WO | 2010011821 A2 | 1/2010 |
| WO | 2010/136493 A1 | 12/2010 |
| WO | 2011/035569 A1 | 3/2011 |

OTHER PUBLICATIONS

De Lombaert et al.; "Non-Peptidic Inhibitors of Neutral Endopeptidase 24.11-2. Design and Pharmacology of Orally Active Phosphonate Prodrugs"; Bioorganic & Medicinal Chemistry Letters; 5(2):151-154 (1995).

Deaton et al.; "Thiol-based angiotensin-converting enzyme 2 inhibitors: P1 modifications for the exploration of the S1 subsite"; Bioorganic & Medicinal Chemistry Letters; 18:732-737 (2008).

Deaton et al.; "Thiol-based angiotensin-converting enzyme 2 inhibitors: P1' modifications for the exploration of the S1' subsite"; Bioorganic & Medicinal Chemistry Letters; 18:1681-1687 (2008).

Hanessian et al.; "Targeting ACE and ECE with dual acting inhibitors"; Bioorganic & Medicinal Chemistry Letters; 18:1058-1062 (2008).

Jeng et al.; "CGS 34226, a thiol-based dual inhibitor of endothelin converting enzyme-I and neutral endopeptidase 24.11"; Clinical Science; 103(Suppl. 48):98S-101S [Printed in Great Britain] (2002).

Park et al., "Therapeutic Potential of Atrial Natriuretic Peptide administration on Peripheral Arterial Diseases", Endocrinology 149(2):483-491 (2008).

Yamahara et al., "Significance and therapeutic potential of the natriuretic peptides/cGMP/cGMP-dependent protein kinase pathway in vascular regeneration", PNAS, 100(6):3404-3409 (2003).

Tokudome et al., "Impaired Recovery of Blood Flow After Hind-limb Ischemia in Mice Lacking Guanytyl Cyclase-A, a receptor for Atrial and Brain Natriuretic Peptides", Arterioscler Thromb Vasc Biol 29:1516-1521 (2009).

Bouboutou et al.; "Bidentate Peptides : Highly Potent New Inhibitors of Enkephalin Degrading Enzymes"; Life Sciences; 35(9):1023-1030 (1984).

Bourdel et al.; "New hydroxamate inhibitors of neurotensin-degrading enzymes—Synthesis and enzyme active-site recognition"; International Journal of Peptide & Protein Research; 48(2):148-155 (1996).

Davies et al.; "First asymmetric synthesis of the Kelatorphan-like enkephalinase inhibitor (1S,2R,2' S)-2-[2'-(N-hydroxycarbamoylmethyl)-3'-phenylpropionylamino]cyclohexane-1-carboxylic acid"; Journal of the Chemical Society, Perkin Transactions 1: Organic and Bio-Organic Chemistry; 17:2629-2634 (1998).

De Lombaert et al.; "Dual Inhibition of Neutral Endopeptidase and Angiotensinconverting Enzyme by N-Phosphonomethyl and N-Carboxyalkyl Dipeptides"; Bioorganic & Medicinal Chemistry Letters; 4(22):2715-2720 (1994).

De Lombaert et al.; Non-Peptidic Inhibitors of Neutral Endopeptidase 24.11 1. Discovery and Optimization of Potency; Bioorganic & Medicinal Chemistry Letters; 5(2):145-150 (1995).

Doulut et al.; "Synthesis and Analgesic Effects of N-[3-[(Hydroxyamino)carbonyl]-1-oxo-2(R)-benzylpropyl]-L-isoleucyl-L-leucine, a New Potent Inhibitor of Multiple Neurotensin/Neuromedin N Degrading Enzymes"; Journal of Medicinal Chemistry; 36(10):1369-1379 (1993).

Fournie-Zaluski et al.; "Synthesis and Biological Properties of Highly Potent Enkephalinase Inhibitors"; Pept., Proc. Eur. Pept. Symp.; 16th; Meeting Date 1980, pp. 476-481 (1981).

Fournie-Zaluski et al.; "Differential Recognition of "Enkephalinase" and Angiotensin-Converting Enzyme by New Carboxyalkyl Inhibitors"; Life Sciences; 31(26):2947-2954 (1982).

Fournie-Zaluski et al.; "New Carboxyalkyl Inhibitors of Brain Enkephalinase: Synthesis, Biological Activity, and Analgesic Properties"; Journal of Medicinal Chemistry; 26(1):60-65 (1983).

Fournie-Zaluski et al.; "Analgesic Effects of Kelatorphan, A New Highly Potent Inhibitor of Multiple Enkephalin Degrading Enzymes"; European Journal of Pharmacology; 102(3-4):525-528 (1984).

Fournie-Zaluski et al.; "Enkephalin-degrading enzyme inhibitors: Crucial role of the C-terminal residue on the inhibitory potencies of retro-hydorxamate dipeptides"; International Journal of Peptide & Protein Research; 33(2): 146-153 (1989).

Fournie-Zaluski et al.; "Development of [125I]RB104, a potent inhibitor of neutral endopeptidase 24.11, and its use in detecting nanogram quantities of the enzyme by "inhibitor gel electrophoresis""; Proceedings of the National Academy of Sciences of the United States of America; 89(14):6388-6392 (1992).

Hachisu et al.; "Relationship Between Enhancement of Morphine Analgesia and Inhibition of Enkephalinase by 2S, 3R 3-Amino-2-Hydroxy-4-Phenylbutanoic Acid Derivatives"; Life Sciences; 30(20):1739-1746 (1982).

Hernandez et al.; "Retro-Inverso Concept Applied to the Complete Inhibitors of Enkephalin-Degrading Enzymes"; Journal of Medicinal Chemistry; 31(9):1825-1831 (1988).

Kanno et al.; "Synthesis and Evaluation of 2-(Biphenylmethyl)Glutaric Acid Amide Derivatives As Neutral Endopeptidase Inhibitors"; Bioorganic & Medicinal Chemistry Letters; 6(13):1487-1490 (1996).

Ksander et al.; "Enkephalinase Inhibitors. 1. 2,4-Dibenzylglutaric Acid Derivatives"; Journal of Medicinal Chemistry; 32(12):2519-2526 (1989).

(56) References Cited

OTHER PUBLICATIONS

Ksander et al.; "Dicarboxylic Acid Dipeptide Neutral Endopeptidase Inhibitors"; Journal of Medicinal Chemistry; 38 (10):1689-1700 (1995).

Matsuoka et al.; "2S,3R 3-Amino-2-Hydroxy-4-Phenylbutanoic Acid Derivatives, Enkephalinase Inhibitors, Augment Met5-Enkephalin-Induced Antinociception"; Japanese Journal of Pharmacology; 46(3):205-210 (1988).

Milhiet et al.; "Increase of Neutral Endopeptidase-24.11 With Cellular Density and Enzyme Modulation With an Inhibitor on Human REH6 Cell Line"; Biochemical Pharmacology; 43(8):1711-1715 (1992).

Roques et al.; "New Enkephalinase Inhibitors as Probes to Differentiate "Enkephalinase" and Angiotensin-Converting-Enzyme Active Sites"; Life Sciences; 31(16-17):1749-1752 (1982).

Tejedor-Real et al.; "Effect of Mixed (RB 38A) and Selective (RB 38B) Inhibitors of Enkephalin Degrading Enzymes on a Model of Depression in the Rat"; Biological Psychiatry; 34(1-2):100-107 (1993).

Wallace et al.; "Design and Synthesis of Potent, Selective Inhibitors of Endothelin-Converting Enzyme"; Journal of Medicinal Chemistry; 41(9):1513-1523 (1998).

Xie et al.; "New inhibitors of enkephalin-degrading enzymes"; Colloque INSERM [2nd Forum Pept.]; 174:349-352 (1989).

Xie et al.; "Inhibitors of the enkephalin degrading enzymes: Modulation of activity of hydroxamate containing compounds by modifications of the C-terminal residue"; International Journal of Peptide & Protein Research; 34 (3):246-255 (1989).

Xie et al.; "New Kelatorphan-Related Inhibitors of Enkephalin Metabolism: Improved Antinociceptive Properties"; Journal of Medicinal Chemistry; 32(7):1497-1503 (1989).

Yao et al.; "Potent P1' Biphenylmethyl Substituted Aggrecanase Inhibitors"; Bioorganic & Medicinal Chemistry Letters; 12:101-104 (2002).

Library compound: RN:144139-09-3.

* cited by examiner

SUBSTITUTED CARBAMOYLMETHYLAMINO ACETIC ACID DERIVATIVES AS NOVEL NEP INHIBITORS

This application is a divisional of U.S. application Ser. No. 13/449,357 filed on Apr. 18, 2012, which is a divisional of U.S. application Ser. No. 12/947,029, filed on Nov. 16, 2010, which claims benefit under 35 U.S.C. §119(e) of U.S. Provisional Application No. 61/263,137, filed Nov. 20, 2009, and U.S. Provisional Application No. 61/359,914, filed on Jun. 30, 2010; the contents of which are incorporated herein by reference in their entirety.

BACKGROUND OF THE INVENTION

Endogenous atrial natriuretic peptides (ANP), also called atrial natriuretic factors (ANF) have diuretic, natriuretic and vasorelaxant functions in mammals. The natural ANF peptides is metabolically inactivated, in particular by a degrading enzyme which has been recognized to correspond to the enzyme neutral endopeptidase (NEP) EC 3.4.24.11, also responsible for e.g. the metabolic inactivation of enkephalins.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEPi) should increase plasma levels of ANP and, hence, are expected to induce natriuretic and diuretic effects.

This enzyme is involved in the breakdown of several bioactive oligopeptides, cleaving peptide bonds on the amino side of hydrophobic amino acid residues. The peptides metabolised include atrial natriuretic peptides (ANP), bombesin, bradykinin, calcitonin gene-related peptide, endothelins, enkephalins, neurotensin, substance P and vasoactive intestinal peptide. Some of these peptides have potent vasodilatory and neurohormone functions, diuretic and natriuretic activity or mediate behaviour effects.

SUMMARY OF THE INVENTION

The aim of the present invention is to provide novel compounds which are useful as neutral endopeptidase inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of this invention are thus particularly useful for the treatment of conditions and disorders responsive to the inhibition of neutral endopeptidase (NEP) EC 3.4.24.11.

The invention pertains to the compounds, methods for using them, and uses thereof as described herein. Examples of compounds of the invention include the compounds according to anyone of Formulae I' and I to IV, or a pharmaceutically acceptable salt thereof and the compounds of the examples.

The invention therefore provides a compound of the formula (I'):

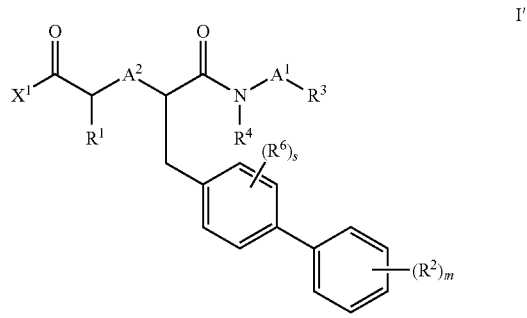

wherein:
$X^1$ is OH, —O—$C_{1-7}$alkyl, —$NR^aR^b$, —$NHS(O)_2$—$C_{1-7}$alkyl or —$NHS(O)_2$-benzyl, wherein $R^a$ and $R^b$ for each occurrence are independently H or $C_{1-7}$alkyl;
$R^1$ is H, $C_{1-6}$ alkyl or $C_{6-10}$-aryl-$C_{1-6}$ alkyl, wherein alkyl is optionally substituted with benzyloxy, hydroxy or $C_{1-6}$ alkoxy;
for each occurrence, $R^2$ is independently $C_{1-6}$-alkoxy, hydroxy, halo, $C_{1-6}$-alkyl, cyano or trifluoromethyl;
$A^2$ is O or $NR^5$;
$R^4$ and $R^6$ are independently H or $C_{1-6}$ alkyl;
$A^1$ is a bond or $C_{1-3}$alkylene chain;
$R^3$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;
$R^6$ for each occurrence is independently halo, hydroxy, $C_{1-7}$alkoxy, halo, $C_{1-7}$alkyl or halo-$C_{1-7}$alkyl; or
$R^4$, $A^1$-$R^3$, together with the nitrogen to which $R^4$ and $A^1$-$R^3$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$ alkyl; and
m is 0 or an integer from 1 to 5;
s is 0 or an integer from 1 to 4; or
a pharmaceutically acceptable salt thereof.

The invention also provides a compound of the formula (I):

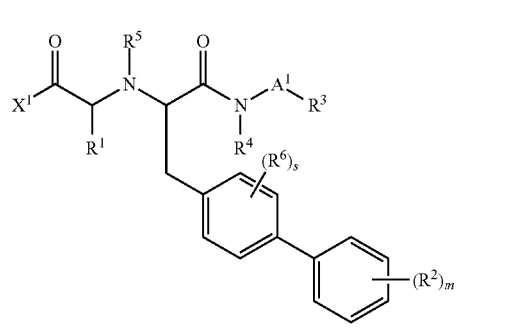

wherein:

$X^1$ represent OH or O—$C_{1-6}$-alkyl;

$R^1$ is H, $C_{1-6}$ alkyl or $C_{6-10}$-aryl-$C_{1-6}$ alkyl;

for each occurrence, $R^2$ is independently $C_{1-6}$-alkoxy, hydroxy, halo, $C_{1-6}$-alkyl, cyano or trifluoromethyl;

$R^4$ and $R^5$ are independently H or $C_{1-6}$ alkyl;

$A^1$ is a bond or $C_{1-3}$alkylene chain;

$R^3$ is a 5- or 6-membered heteroaryl, $C_{6-10}$-aryl or $C_{3-7}$-cycloalkyl, wherein each heteroaryl, aryl or cycloalkyl are optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^6$ for each occurrence is independently halo, hydroxy, $C_{1-7}$alkoxy, halo, $C_{1-7}$alkyl or halo-$C_{1-7}$akyl; or $R^4, A^1$-$R^3$, together with the nitrogen to which $R^4$ and $A^1$-$R^3$ are attached, form a 4- to 7-membered heterocyclyl or a 5- to 6-membered heteroaryl, each of which is optionally substituted with one or more groups independently selected from the group consisting of $C_{1-6}$alkyl, halo, halo$C_{1-6}$alkyl, $C_{1-6}$alkoxy, hydroxy, $CO_2H$ and $CO_2C_{1-6}$ alkyl; and m is 0 or an integer from 1 to 5;

s is 0 or an integer from 1 to 4; or a pharmaceutically acceptable salt thereof.

The compounds of the invention, by inhibiting the neutral endopeptidase EC.3.4.24.11, can potentiate the biological effects of bioactive peptides. Thus, in particular the compounds have utility in the treatment of a number of disorders, including hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menières disease, hyperaldosteroneism (primary and secondary) and hypercalciuria, ascites. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of menstrual disorders, preterm labour, pre-eclampsia, endometriosis, and reproductive disorders (especially male and female infertility, polycystic ovarian syndrome, implantation failure). Also the compounds of the invention should treat asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and athereosclerosis, male and female sexual dysfunction.

In a preferred embodiment the compounds of the invention are useful in the treatment of cardiovascular disorders.

In another embodiment, the invention pertains to a method for treating a disorders or diseases responsive to the inhibition of neutral endopeptidase EC 3.4. 24.11 (NEP), in a subject in need of such treatment, comprising: administering to the subject an effective amount of a compound according to anyone of Formulae I-IV, or a pharmaceutically acceptable salt thereof, such that the disorder or disease responsive to the inhibition of neutral endopeptidase EC 3.4. 24.11 (NEP) in the subject is treated.

In yet another embodiment, the invention pertains to pharmaceutical compositions, comprising a compound according to anyone of Formulae I-IV, or a pharmaceutically acceptable salt thereof, and one or more pharmaceutically acceptable carriers.

In still another embodiment, the invention pertains to combinations including, a compound according to anyone of Formulae I-IV, or a pharmaceutically acceptable salt thereof, and pharmaceutical combinations of one or more therapeutically active agents.

In another embodiment, the invention pertains to a method for inhibiting neutral endopeptidase EC 3.4. 24.11 in a subject in need thereof, comprising: administering to the subject a therapeutically effective amount of a compound according to anyone of Formulae I-IV, or a pharmaceutically acceptable salt thereof, such that neutral endopeptidase EC 3.4. 24.11 is inhibited.

DETAILED DESCRIPTION OF THE INVENTION

Definition

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 6 carbon atoms, and more preferably 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-6}$alkyl" refers to a hydrocarbon having from one to six carbon atoms. The term "alkylene" refers to a divalent alkyl radical, wherein alkyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichioropropyl. A perhaloalkyl refers to an alkyl having all hydrogen atoms replaced with halo atoms. The term "halo-$C_{1-6}$alkyl" refers to a hydrocarbon having one to six carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

As used herein, the term "cycloalkyl" refers to saturated or partially unsaturated monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$cycloakyl" refers to a cyclic hydrocarbon groups having 3 to 7 carbon atoms.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "$C_{6-10}$aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-CH$_2$CH$_2$—. The term "$C_{6-10}$aryl-$C_{1-6}$alkyl" refers to a hydrocarbon having one to six carbon atoms, which hydrocarbon is substituted with an aryl having 6 to 10 carbon atoms.

The term "Heteroaryl" includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl rings, where the radical or point of attachment is on the heteroaromatic ring or on the fused aryl ring. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl. When a heteroaryl moiety is substituted with hydroxy, the invention also pertains to its oxo tautomeric. For example, an oxadiazole substituted with hydroxy also includes oxo-oxadiazole also known as oxadiazolone. The tautomerisation is represented as follow:

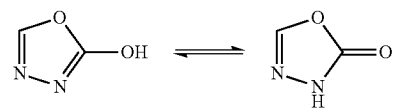

As used herein, the term "heterocyclyl" or "heterocyclo" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "halogen" includes fluorine, bromine, chlorine and iodine. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment the heteroatoms is selected from N, O and S.

Compound of the Invention

Various embodiments of the invention are described herein. It will be recognized that features specified in each embodiment may be combined with other specified features to provide further embodiments.

Certain compounds of Formula I' or I include compounds of Formula II:

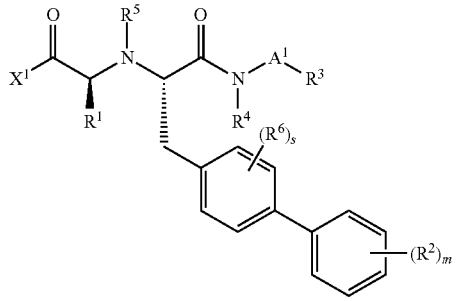

or a pharmaceutically acceptable salt thereof, wherein $R^1$, $R^2$, $R^3$, $R^4$, $R^5$, $R^6$, $X^1$, $A^1$, s and m have the definition of Formula I, supra.

In one embodiment the invention pertains to compounds of formula I', I or II wherein:

$X^1$ represent OH or O—$C_{1-6}$-alkyl;

$R^1$ is H or $C_{1-6}$ alkyl;

for each occurrence, $R^2$ is independently $C_{1-6}$-alkoxy, hydroxy, halo, $C_{1-6}$-alkyl, cyano or trifluoromethyl;

$R^4$ and $R^5$ are independently H or $C_{1-6}$ alkyl;

$A^1$ is a bond or $C_{1-3}$alkylene chain;

$R^3$ is a 5- or 6-membered heteroaryl or $C_{6-10}$-aryl, wherein each heteroaryl and aryl are optionally substituted with one or more substituents independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^6$ for each occurrence is independently halo, hydroxy, $C_{1-7}$alkoxy, halo, $C_{1-7}$alkyl or halo-$C_{1-7}$alkyl;

m is 0 or an integer from 1 to 5;

s is 0 or an integer from 1 to 4; or a pharmaceutically acceptable salt thereof.

In another embodiment the invention pertains to compounds of formula I', I or II wherein:

$X^1$ represent OH or O—$C_{1-6}$-alkyl;

$R^1$ is H or $C_{1-6}$ alkyl;

for each occurrence, $R^2$ is independently $C_{1-6}$-alkoxy, hydroxy, halo, $C_{1-6}$-alkyl, cyano or trifluoromethyl;

$R^4$ and $R^5$ are independently H or $C_{1-6}$ alkyl;

$A^1$ is a bond or $C_{1-3}$alkylene chain;

$R^3$ is a 5- or 6-membered heteroaryl optionally substituted with one or more substituents independently selected from the group consisting of $C_{1-6}$alkyl, halo, halo$C_{1-6}$alkyl, $C_{1-6}$alkoxy, hydroxy, $CO_2H$ and $CO_2C_{1-6}$alkyl;

$R^6$ for each occurrence is independently halo, hydroxy, $C_{1-7}$alkoxy, halo, $C_{1-7}$alkyl or halo-$C_{1-7}$alkyl;

m is 0 or an integer from 1 to 5;

s is 0 or an integer from 1 to 4; or a pharmaceutically acceptable salt thereof.

Certain compounds of Formula I' or I include compounds of Formula III:

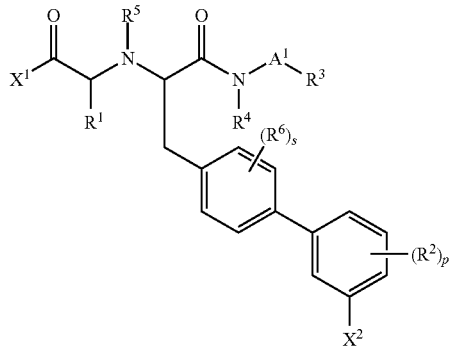

or a pharmaceutically acceptable salt thereof, wherein $R^1$, $R^2$, $R^3$, $R^4$, $R^5$, $R^6$, $X^1$, $A^1$ and s have the definition of Formula I, supra and $X^2$ is halo and p is 0 or an integer from 1 to 4.

Certain compounds of Formula I', I, II or III include compounds of Formula IV:

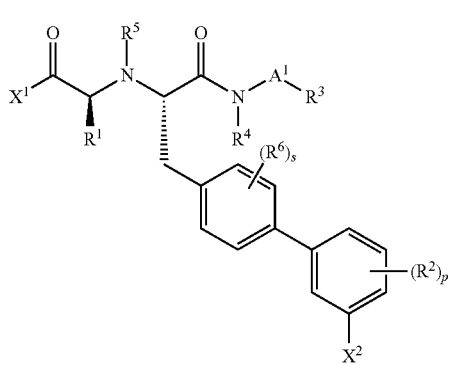

or a pharmaceutically acceptable salt thereof, wherein $R^1$, $R^2$, $R^3$, $R^4$, $R^5$, $R^6$, $X^1$, $A^1$, $X^2$, s and p have the definition of Formulae I, II and III, supra.

In one embodiment, the invention pertains to compounds of Formula III or IV, or a pharmaceutically acceptable salt thereof, wherein $X^2$ is a Cl. In a further aspect of this embodiment p is 0.

The following embodiments can be used independently, collectively or in any combination or sub-combination:

In one embodiment, the invention pertains to compounds according to anyone of Formulae I' and I to IV, or any of any other classes and subclasses described supra, or a pharmaceutically acceptable salt thereof, wherein $A^1$ is a bond or $CH_2$. In a further embodiment $A^1$ is a bond.

In another embodiment, the invention pertains to compounds according to anyone of Formulae I' and I to IV, or any of any other classes and subclasses described supra, or a pharmaceutically acceptable salt thereof, wherein $R^3$ is an optionally substituted 5- or 6-membered heteroaryl. In one aspect of this embodiment, $R^3$ is a 6-membered ring heteroaryl selected from the group consisting of pyrazine, pyridine, pyrimidine, pyranone (e.g. optionally substituted pyran-4-one, pyran-2-one such as 3-hydroxy-pyran-4-one, 3-hydroxy-pyran-2-one), pyrimidinone and pyridinone (e.g. optionally substituted pyridin-4-one or pyridin-2-one such as for example 3-hydroxy-1-methyl-pyridin-4-one or 1-benzyl-pyridin-2-one). In another aspect of this embodiment $R^3$ is a 5-membered ring heteroaryl selected from the group consisting of oxazole, pyrrole, pyrazole, isooxazole, triazole, tetrazole, oxadiazole (e.g. 1-oxa-3,4-diazole, 1-oxa-2,4-diazole), oxadiazolone (e.g. oxadiazol-2-one), thiazole, isothiazole, thiophene, imidazole and thiadiazole. Other representative examples of $R^3$ are oxazolone, thiazolone, oxadiazolone triazolone, oxazolone, imidazolone, pyrazolone. In a further embodiment, the optional substituents on the heteroaryl are independently $C_{1-6}$alkyl, halo, halo$C_{1-6}$alkyl, $C_{1-6}$alkoxy, hydroxy, $CO_2H$ or $CO_2C_{1-6}$alkyl.

In another aspect of the above embodiment, the invention pertains to compounds according to anyone of Formulae I' and I to IV, or any of any other classes and subclasses described supra, or a pharmaceutically acceptable salt thereof, wherein $R^3$ is tetrazole.

In another embodiment, the invention pertains to compounds according to anyone of Formulae I' and I to IV, or any of any other classes and subclasses described supra, or a pharmaceutically acceptable salt thereof, wherein $R^3$ is an optionally substituted phenyl. In a further embodiment, the optional substituents on phenyl are independently $C_{1-6}$alkyl, halo, halo$C_{1-6}$alkyl, $C_{1-6}$alkoxy, hydroxy, $CO_2H$ or $CO_2C_{1-6}$alkyl. In a further embodiment, phenyl is substituted with $CO_2H$ and further optionally substituted.

In another embodiment, the invention pertains to compounds according to anyone of Formulae I' and I to IV or any of any other classes and subclasses described supra, or a pharmaceutically acceptable salt thereof, wherein $R^1$ is $C_{1-6}$ alkyl (i.e. methyl, ethyl, propyl, isopropyl).

In another embodiment, the invention pertains to compounds according to anyone of Formulae I' and I to IV or any of any other classes and subclasses described supra, or a pharmaceutically acceptable salt thereof, wherein $R^4$ is H.

In another embodiment, the invention pertains to compounds according to anyone of Formulae I' and I to IV or any of any other classes and subclasses described supra, or a pharmaceutically acceptable salt thereof, wherein $R^5$ is H.

In another embodiment, the invention pertains to compounds according to anyone of Formulae I' and I to IV or any of any other classes and subclasses described supra, or a pharmaceutically acceptable salt thereof, wherein s is 0.

In another embodiment $R^1$, $R^2$, $R^3$, $R^4$, $R^5$, $R^6$, $X^1$, $A^1$, $X^2$, m, s and p groups are those defined by the $R^1$, $R^2$, $R^3$, $R^4$, $R^5$, $R^6$, $X^1$, $A^1$, $X^2$, m, s and p groups in the Examples section below.

In another embodiment individual compounds according to the invention are those listed in the Examples section below or a pharmaceutically acceptable salt thereof.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atom may be enriched in $^2$H; or/and one or more carbon atom may be enriched in $^{11}$C, $^{13}$C or $^{14}$C; or/and one or more nitrogen may be enriched in $^{14}$N. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae I to IV. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds of formulae I to IV can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I', I, II, III or IV that contain groups capable of acting as donors and/or acceptors for hydrogen bonds may be capable of forming co-crystals with suitable co-crystal formers. These co-crystals may be prepared from compounds of formula I', I, II, III, IV or V by known co-crystal forming procedures. Such procedures include grinding, heating, co-subliming, co-melting, or contacting in solution compounds of formula I', I, II, III or IV with the co-crystal former under crystallization conditions and isolating co-crystals thereby formed. Suitable co-crystal formers include those described in WO 2004/078163. Hence the invention further provides co-crystals comprising a compound of formula I', I, II, III or IV, or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease or a symptom thereof (i) ameliorated by the inhibition of neutral endopeptidase EC 3.4. 24.11 or (ii) associated with neutral endopeptidase EC 3.4. 24.11 activity, or (iii) characterized by abnormal activity of neutral endopeptidase EC 3.4. 24.11; or (2) reduce or inhibit the activity of neutral endopeptidase EC 3.4. 24.11; or (3) reduce or inhibit the expression of neutral endopeptidase EC 3.4. 24.11. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of neutral endopeptidase EC 3.4. 24.11; or at least partially reduce or inhibit the expression of neutral endopeptidase EC 3.4. 24.11

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Scheme:

The compounds of the invention can be synthesized using the methods described in the following schemes, examples, and by using art recognized techniques. All compounds described herein are included in the invention as compounds. Compounds of the invention may be synthesized according to at least one of the methods described in schemes 1-3.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds according to of formulae I to IV can be prepared according to the Schemes 1 to 7 provided infra.

The compounds of the invention of Formula I' or I wherein $X^1$ is hydroxy can be prepared by hydrolysis of intermediate A wherein $A^1$, $R^1$, $R^2$, $R^3$, $R^4$ and m have the definition of Formula I' or I, supra; and $P^1$ is an appropriate protecting groups selected from, but not limited to, methyl, ethyl, or tert-butyl, or methoxybenzyl, or benzyl.

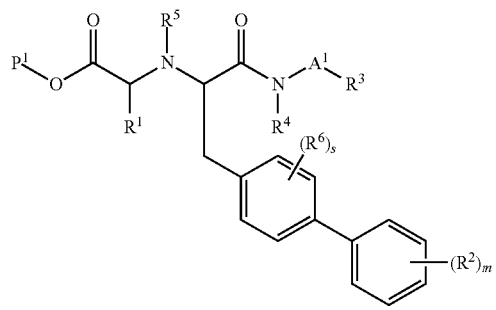

Intermediate A

Standard methods can be applied for the hydrolysis of the intermediate A using a base selected from, but not limited to, NaOH, KOH, or LiOH, or an acid selected from, but not limited to, TFA, HCl, or BCl$_3$. When $P^1$ is benzyl or methoxybenzyl, a preferable method of the deprotection is hydrogenation in the presence of a catalyst such as, but not limited to, palladium-on-carbon.

In some cases, the hydrolysis of intermediate A is not required; for example when intermediate A is a compound of the invention of Formula I' or I wherein $X^1$ is O-alkyl.

Scheme 1 illustrates the synthesis of intermediate A. The intermediate A can be prepared according to the following general procedures described in Scheme 1 wherein $A^1$, $P^1$, $R^1$, $R^2$, $R^3$, $R^4$, $R^5$, $R^6$, s and m are as previously defined.

Scheme 1

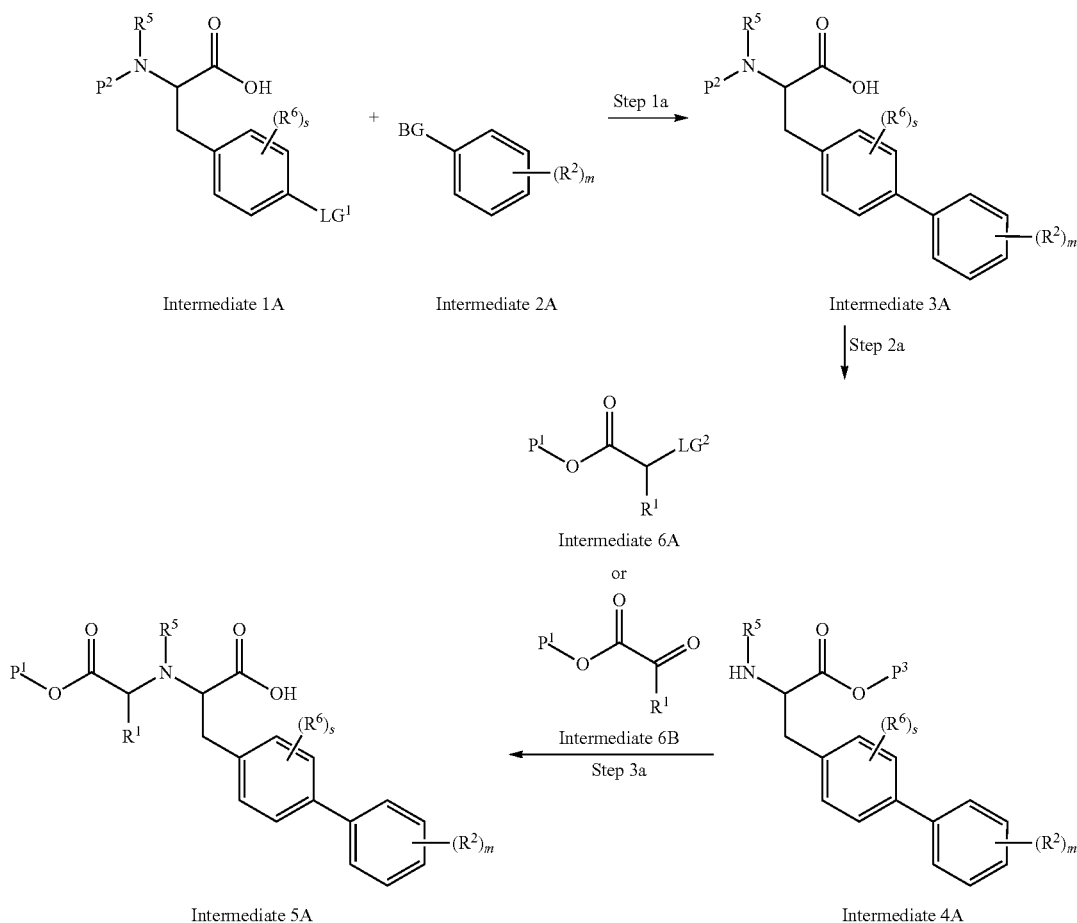

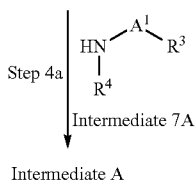

In step 1a, the intermediate 3A can be prepared by cross-coupling of an intermediate 1A wherein $P^2$ is an appropriate protecting groups selected from, but not limited to, t-butoxycarbony, benzyloxycarbony, fluorenylmethyloxycarbonyl, benzyl, or methoxybenzyl and wherein $LG^1$ is a leaving group selected from, but not limited to, halo (e.g. bromo, chloro, or iodo) or trifluoromethanesulfonyloxy with an intermediate 2A wherein $R^2$ and m are as previously described and wherein BG is an appropriate groups selected from, but not limited to, boronic acid, trifluoroborate or boronic ester. Known coupling methods may be applied including Suzuki-Miyaura coupling of the intermediate 1A with the intermediate 2A using palladium species such as, but not limited to, $Pd(PPh_3)_4$, $PdCl_2(dppf)$, $Pd(PPh_3)_2Cl_2$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

In step 2a, the intermediate 4A can be prepared by appropriate protection of an intermediate 3A wherein $P^3$ is a protection group such as, but not limited to, t-butyl, methyl, benzyl, fluorenylmethyl, allyl or methoxybenzyl; followed by an appropriate deprotection of the $P^2$ group.

In step 3a, the intermediate 5A can be prepared by reacting an intermediate 4A wherein $R^2$, $R^5$, $R^6$, s, m, and $P^3$ are as previously defined with an intermediate 6A wherein $R^1$ and $P^1$ are as previously defined above and wherein $LG^2$ is a leaving group selected from, but not limited to, trifluoromethansulfonyloxy, toluenesulfonyloxy, methansulfonyloxy, iodo, bromo, and chloro, followed by deprotection of the $P^3$ using an appropriate method. Alternatively, the intermediates 5A can be prepared by reacting an intermediate 4A with an intermediate 6B wherein $R^1$ and $P^1$ are as defined above, followed by deprotection of the $P^3$ using an appropriate method. Known coupling methods may be applied including alkylation of the intermediate 4A with the intermediate 6A using a base such as, but not limited to, tertiary amine (e.g. triethylamine or N,N-diisopropyl ethylamine), pyridine, or $K_2CO_3$; or reductive amination condition of intermediate 4A with the intermediate 6B, under condition such as hydrogenation in the presence of a catalyst such as palladium-on-carbon or reduction using a reductive reagent (e.g. $NaBH_4$, $NaBH(OAc)_3$, or $NaBH_3CN$) in the presence of or absence of an acid such as acetic acid, TFA, or $Ti(i-PrO)_4$.

In step 4a, the intermediate A can be prepared by coupling an intermediate 5A wherein $P^1$, $R^1$, $R^2$, $R^5$, $R^6$, s and m are as previously described with an intermediate 7A wherein $A^1$, $R^3$, and $R^4$ are previously described. Known coupling methods may be applied including, but not limited to, conversion of the intermediate 5A to a corresponding oxazolidine-2,5-dione, using reagents such as triphosgene, carbonyldiimidazole, 4-nitrophenyl chloroformate, or disuccinimidyl carbonate, conversion of the intermediate 5A to a corresponding acid halide, using reagents such as thionyl chloride or oxalyl chloride, or conversion of the intermediate 5A to a corresponding mixed anhydride using reagents such as ClC(O)O-isobutyl, 2,4,6-trichlorobenzoyl chloride or propyl phosphonic acid anhydride cyclic trimer (T3P), followed by reaction of the oxazolidine-2,5-dione, the acid halide, or the mixed anhydride with the intermediate 7A in a presence or absence of a base such as tertiary amine (e.g. triethylamine or N,N-diisoproplyl ethylamine) or $K_2CO_3$. Alternatively, the intermediate 5A can be coupled with the intermediate 7A using peptide condensation reagents including, but not limited to, dicyclohexylcarbodiimide (DCC), diisopropylcarbodiimide (DIC), 1-ethyl-3-(3-dimethyllaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine.

Scheme 2 illustrates the synthesis of Intermediate 5A. The intermediate 5A can also be prepared according to the following procedures described in Scheme 2 wherein BG, $LG^1$, $LG^2$, $P^1$, $P^3$, $R^1$, $R^2$, and m are as previously defined.

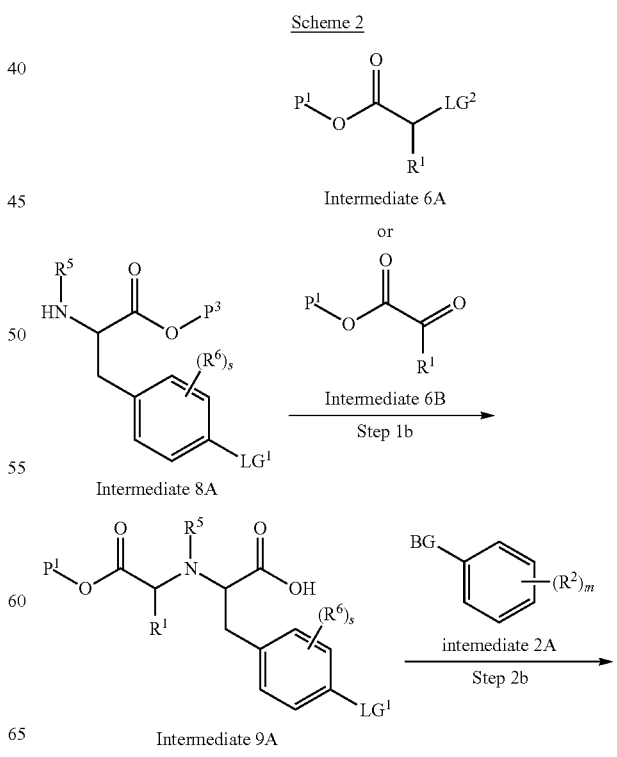

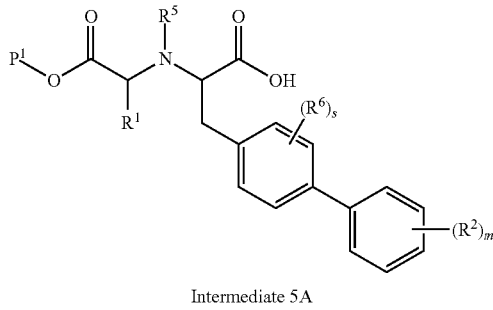

Intermediate 5A

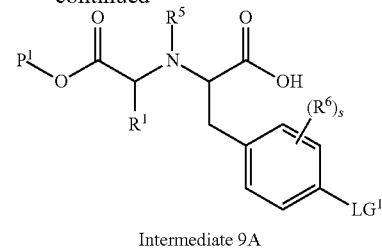

Intermediate 9A in step 1b, the intermediate 9A can be prepared by reacting an intermediate 8A where in $LG^1$, $R^5$, $R^6$, s and $P^3$ are previously described with an intermediate 6A wherein $R^1$, $P^1$, and $LG^2$ are as previously described, followed by an appropriate deprotection of the protecting group $P^3$. Alternatively, the intermediates 9A can be prepared by reacting an intermediate 8A with an intermediate 6B wherein $P^1$ and $R^1$ are as previously described, followed by an appropriate deprotection of the protecting group $P^3$. Known reaction methods may be applied including alkylation of the intermediate 8A with the intermediate 6A using a base such as, but not limited to, tertiary amine (e.g. triethylamine or N,N-diisoproplyl ethylamine), pyridine, or $K_2CO_3$, or reductive amination condition of intermediate 8A with the intermediate 6B, under condition such as hydrogenation in the presence of a catalyst such as palladium-on-carbon or reduction using a reducing reagent (e.g. $NaBH_4$, $NaBH(OAc)_3$, or $NaBH_3CN$) in the presence of or absence of an acid such as acetic acid, TFA, or $Ti(i-PrO)_4$.

In step 2b, the intermediate 5A can be prepared by cross-coupling of an intermediate 9A wherein $LG^1$, $P^1$, $R^5$, $R^6$, $R^1$ and s with an intermediate 2A wherein BG, m, and $R^2$ are as previously described. Known coupling methods may be applied including Suzuki-Miyaura coupling of the intermediate 9A with the intermediate 2A using palladium species such as, but not limited to, $Pd(PPh_3)_4$, $PdCl_2(dppf)$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

The intermediates 9A can also be prepared according to the following general procedure described in Scheme 3 wherein $LG^1$, $P^1$, $P^3$, $R^5$, $R^6$, $R^1$ and s are as previously described.

Scheme 3

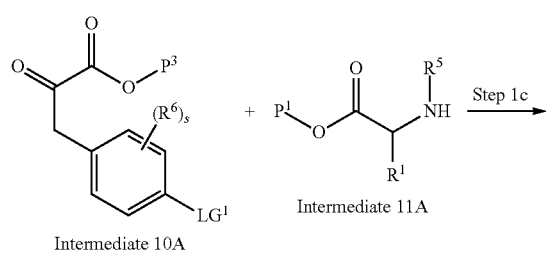

In step 1c, the intermediate 9A can be prepared by reductive amination of the intermediate 10A wherein $LG^1$, $R^6$, s and $P^3$ are as previously described with the intermediate 11A wherein $P^1$, $R^5$ and $R^1$ are as previously described. Known reductive amination methods may be applied including a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i-PrO)_4$. The intermediate 10A can be prepared according to the reported procedure. The illustrative example of this chemistry is outlined in WO 2006015885.

The intermediate 5A can also be prepared according to the following general procedures described in Scheme 4 wherein m, $P^1$, $P^3$, $R^1$, and $R^2$ are as previously described.

Scheme 4

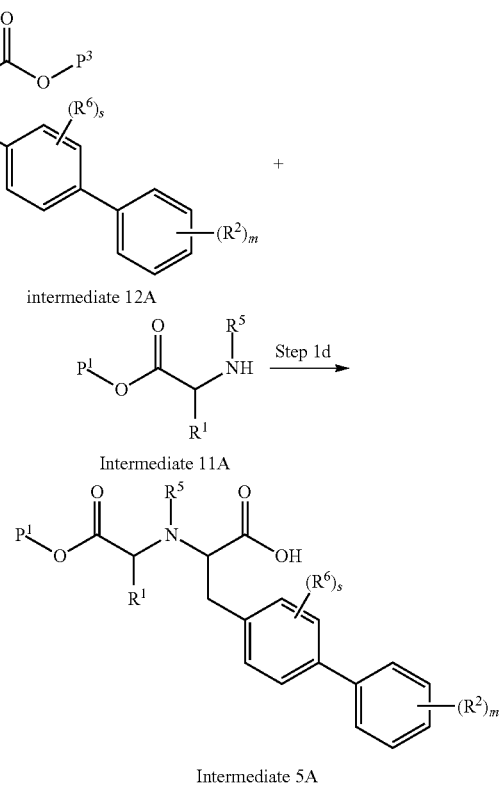

In step 1d, the intermediate 5A can be prepared by reductive amination of the intermediate 12A wherein m, $P^3$, $R^5$, $R^6$, s, m and $R^2$ are as previously described with the intermediate 11A wherein $P^1$, $R^5$ and $R^1$ are as previously described.

Known reductive amination methods may be applied including a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i-PrO)_4$. The intermediates 12A can be prepared according to the reported procedure. The illustrative example of this chemistry is outlined in WO 2006015885.

The intermediate A can also be prepared according to the following procedures described in Scheme 5 wherein $A^1$, $LG^2$, $P^1$, $P^2$, $R^1$, $R^2$, $R^3$, $R^4$, $R^5$, $R^6$, s and m are as previously described.

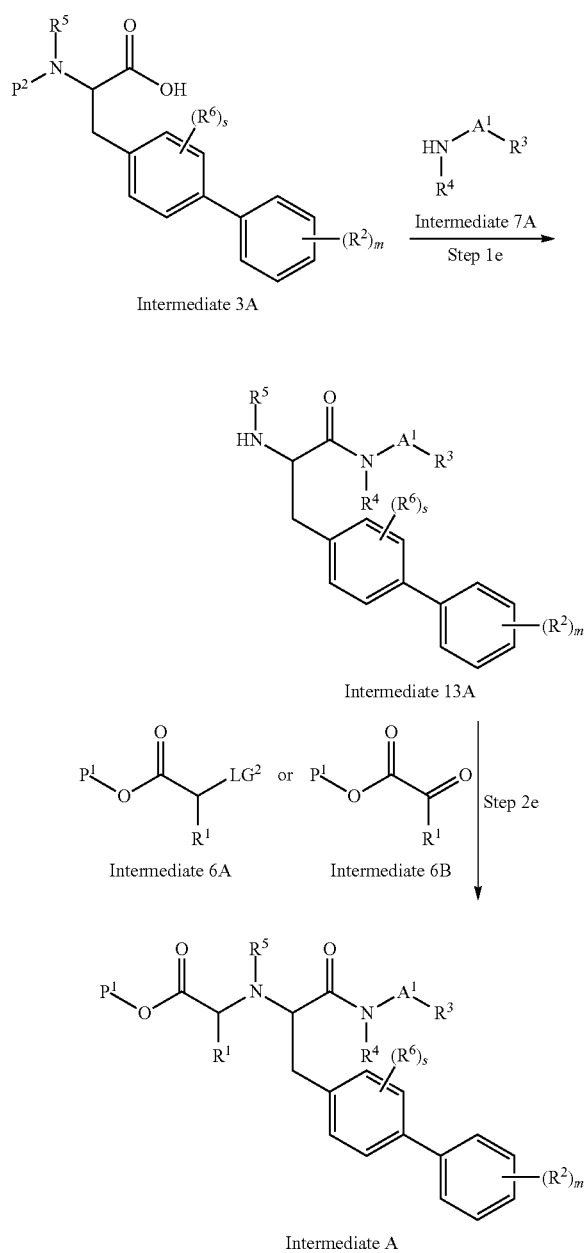

In step 1e, the intermediate 13A can be prepared by coupling an intermediate 3A with an intermediate 7A. Known coupling methods may be applied including, but not limited to, conversion of the intermediate 3A to a corresponding oxazolidine-2,5-dione, using reagents such as triphosgene, carbonyldiimidazole, 4-nitrophenyl chloroformate, or disuccinimidyl carbonate, conversion of the intermediate 3A to a corresponding acid halide, using reagents such as thionyl chloride or oxalyl chloride, or conversion of the intermediate 3A to a corresponding mixed anhydride using reagents such as ClC(O)O-isobutyl or 2,4,6-trichlorobenzoyl chloride, followed by reaction of the oxazolidine-2,5-dione, the acid halide, or the mixed anhydride with the intermediate 7A in a presence or absence of a base such as tertiary amine (e.g. triethylamine or N,N-diisoproplyl ethylamine) or $K_2CO_3$ and an appropriate deprotection of $P^2$ protecting group. Alternatively, the intermediate 3A can be coupled with the intermediate 7A using peptide condensation reagents including, but not limited to, dicyclohexylcarbodiimide (DCC), diisopropylcarbodiimide (DIC), 1-ethyl-3-(3-dimethylaminopropyl) carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine followed by an appropriate deprotection of $P^2$ protecting group.

In step 2e, the intermediate A can be prepared by reacting an intermediate 13A with an intermediate 6A wherein $LG^2$ is as previously described. Alternatively, the intermediates A can be prepared by reacting an intermediate 13A with an intermediate 6B. Known reaction methods may be applied including alkylation of the intermediate 13A with the intermediate 6A using a base such as, but not limited to, tertiary amine (e.g. triethylamine or N,N-diisoproplylethylamine), pyridine, or $K_2CO_3$ or reductive amination of the intermediate 13A with the intermediate 6B under a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i-PrO)_4$.

The intermediates A can also be prepared according to the following procedures described in Scheme 6 wherein $A^1$, BG, $LG^1$, $P^1$, $R^1$, $R^2$, $R^3$, $R^4$, $R^5$, $R^6$, s and m are as previously described.

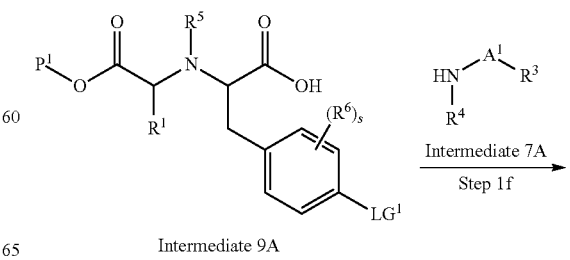

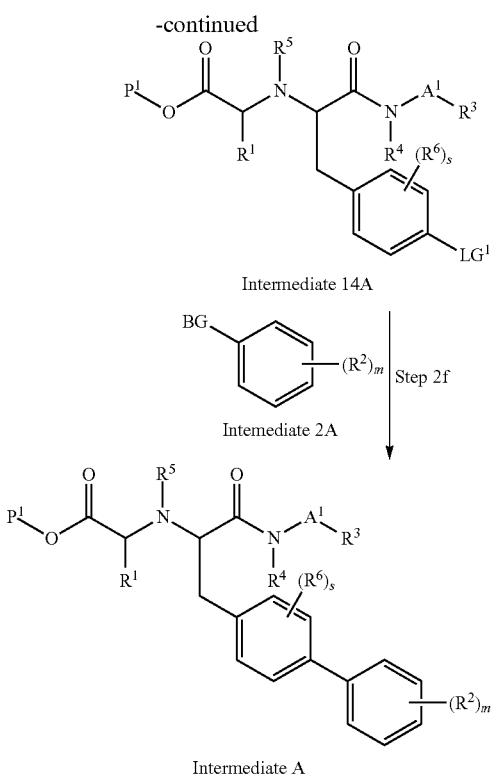

Intermediate 14A

Intemediate 2A

Intermediate A

In step 1f, an intermediate 14A can be prepared by coupling the intermediate 9A wherein $LG^1$, $P^1$, $R^5$, $R^6$, m, s and $R^1$ are as previously described with an intermediate 7A. Known coupling methods may be applied including, but not limited to, conversion of the intermediate 9A to a corresponding oxazolidine-2,5-dione, using reagents such as triphosgene, carbonyldiimidazole, 4-nitrophenyl chloroformate, or disuccinimidyl carbonate, conversion of the intermediate 9A to a corresponding acid halide, using reagents such as thionyl chloride or oxalyl chloride, or conversion of the intermediate 9A to a corresponding mixed anhydride using reagents such as ClC(O)O-isobutyl or 2,4,6-trichlorobenzoyl chloride, followed by reaction of the oxazolidine-2,5-dione, the acid halide, or the mixed anhydride with the intermediate 7A in a presence or absence of a base such as tertiary amine (e.g. triethylamine or N,N-diisoproplylethylamine) or $K_2CO_3$. Alternatively, the intermediate 9A can be coupled with the intermediate 7A using peptide condensation reagents including, but not limited to, dicyclohexylcarbodiimide (DCC), diisopropylcarbodiimide (DC), 1-ethyl-3-(3-dimethyllaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonim hexafluorophosphate (BOP) in presence of or absence of a reagent such as 1-hydroxybenzotriazole, 1-hydroxy-7-azabenzotriazole, or dimethylaminopyridine.

In step 2f, the intermediate A can be prepared by cross-coupling of an intermediate 14A wherein $A^1$, $LG^1$, $P^1$, $R^1$, $R^3$, $R^5$, $R^6$, m, s and $R^4$ are as previously described with an intermediate 2A wherein $R^2$, m, and BG are as previously described. Known coupling methods may be applied including Suzuki-Miyaura coupling of the intermediate 14A with the intermediate 2A using palladium species such as, but not limited to, $Pd(PPh_3)_4$, $PdCl_2(dppf)$, or $Pd(OAc)_2$ with a phosphine ligand such as $PPh_3$, dppf, $PCy_3$, or $P(t-Bu)_3$ and a base such as, but not limited to, $Na_2CO_3$, $K_3PO_4$, $K_2CO_3$, KF, CsF, NaO-t-Bu, or KO-t-Bu.

The intermediates 14A can also be prepared according to the following procedures described in Scheme 7 wherein $A^1$, $LG^1$, $LG^2$, $P^1$, $P^2$, $R^1$, $R^2$, $R^3$, $R^4$, $R^5$, $R^6$, s and m are as previously described.

Scheme 7

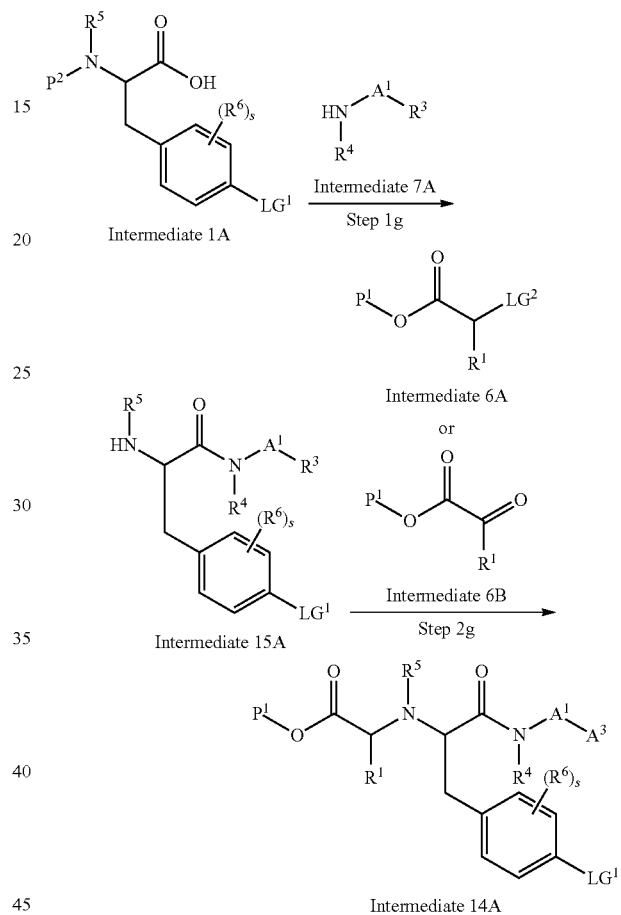

Intermediate 1A

Intermediate 6A or

Intermediate 6B

Intermediate 15A

Intermediate 14A

In step 1g, an intermediate 15A can be prepared by coupling the intermediate 1A wherein $P^2$, $R^5$, $R^6$, s and $LG^1$ are as previously described with an intermediate 7A wherein $A^1$, $R^3$, and $R^4$ are as previously described followed by an appropriate deprotection of the protecting group $P^2$. Known coupling methods may be applied including, but not limited to, conversion of the intermediate 1A to corresponding oxazolidine-2,5-dione, using reagents such as triphosgene, carbonyldiimidazole, 4-nitrophenyl chloroformate, or disuccinimidyl carbonate, conversion of the intermediate 1A to corresponding acid halide, using reagents such as thionyl chloride or oxalyl chloride, or conversion of the intermediate 1A to corresponding mixed anhydride using reagents such as ClC(O) O-isobutyl or 2,4,6-trichlorobenzoyl chloride, followed by reaction of the oxazolidine-2,5-dione, the acid halide, or the mixed anhydride with the intermediate 7A in a presence or absence of a base such as tertiary amine (e.g. triethylamine or N,N-diisoproplyl ethylamine) or $K_2CO_3$. Alternatively, the intermediate 1A can be coupled with the intermediate 7A using peptide condensation reagents including, but not limited to, dicyclohexylcarbodiimide (DCC), diisopropylcarbodiimide (DIC), 1-ethyl-3-(3-dimethylaminopropyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine.

In step 2g, the intermediate 14A can be prepared by reacting an intermediate 15A wherein $A^1$, $LG^1$, $R^3$, $R^5$, $R^6$, s and $R^4$ are as previously defined with an intermediate 6A wherein $R^1$, $P^1$, and $LG^2$ are as previously defined. Alternatively, the intermediates 14A can be prepared by reacting an intermediate 15A wherein $A^1$, $LG^1$, $R^3$, $R^5$, $R^6$, s and $R^4$ are as previously defined with an intermediate 6B wherein $R^1$ and Ware as previously described. Known reaction methods may be applied including alkylation of the intermediate 15A with the intermediate 6A using a base such as, but not limited to, tertiary amine (e.g. triethylamine or N,N-diisoproplyl ethylamine), pyridine, or $K_2CO_3$ or reductive amination of the intermediate 15A with the intermediate 6B under a condition such as, but not limited to, hydrogenation in the presence of a catalyst such as palladium-on-carbon or reduction using a reagent such as, but not limited to, $NaBH_4$, $NaBH(OAc)_3$, or $NaBH_3CN$ in the presence of or absence of an acid such as acetic acid, TFA, or $Ti(i-PrO)_4$.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention or a pharmaceutically acceptable salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I to IV, or a pharmaceutically acceptable salt thereof, in free form or in pharmaceutically acceptable salt form, exhibit valuable pharmacological properties, e.g. neutral endopeptidase EC 3.4. 24.11 modulating properties, e.g. as indicated in in vitro and in vivo tests as provided in the next sections and are therefore indicated for therapy.

Compounds of the invention or a pharmaceutically acceptable salt thereof, may be useful in the treatment of an indication selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunctions, hyperreninaemia, cystic fibrosis, restenosis, type-2 diabetes, metabolic syndrome, diabetic complications and atherosclerosis, male and female sexual dysfunction. Thus, as a further embodiment, the present invention provides the use of a compound of formula I', I, II, III or IV, or a pharmaceutically acceptable salt thereof. In a further embodiment, the therapy is selected from a disease which is associated with neutral endopeptidase EC 3.4. 24.11 activity. In another embodiment, the disease is selected from the afore-mentioned list, suitably hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency, renal failure (including edema and salt retension), diabetic nephropathy, non-diabetic nephropathy, type-2 diabetis, and diabetic complications and most suitably cardiovascular disorders, such as hypertension, renal insufficiency including edema and congestive heart failure.

Thus, as a further embodiment, the present invention provides the use of a compound of formula I' I, II, III or IV, or a pharmaceutically acceptable salt thereof, in therapy. In a further embodiment, the therapy is selected from a disease which may be treated by inhibiting neutral endopeptidase EC. 3.4. 24.11. activity.

In another embodiment, the invention provides a method of treating a disease which is associated with neutral endopeptidase EC 3.4. 24.11 activity comprising administration of a therapeutically acceptable amount of a compound of formula I', I, II, III or IV, or a pharmaceutically acceptable salt thereof. In a further embodiment, the disease is selected from the afore-mentioned list, suitably hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency, renal failure (including edema and salt retension), diabetic nephropathy, non-diabetic nephropathy, type-2 diabetes, and diabetic complications and most suitably cardiovascular disorders, such as hypertension, renal insufficiency including edema and congestive heart failure.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods and/or by the following in vitro & in vivo methods well-described in the art. See A fluorescence lifetime-based assay for protease inhibitor profiling on human kallikrein 7 Doering K, Meder G, Hinnenberger M, Woelcke J, Mayr L M, Hassiepen U Biomol Screen. 2009 January; 14(1):1-9.

In particular, the in vitro inhibition of recombinant human neutral endopeptidase (NEP, EC 3.424.11) can be determined as follows:

Recombinant human neutral endopeptidase (expressed in insect cells and purified using standard methods, final concentration 7 pM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys (PT14)-Arg-Arg-Leu-Trp-OH to a final concentration of 0.7 µM. Substrate hydrolysis leads to an increase fluorescence lifetime (FLT) of PT14 measured by the means of a FLT reader as described by Doering et al. (2009). The effect of the compound on the enzymatic activity was determined after 1 hour (t=60 min) incubation at room temperature. The IC50 values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory efficacy in accordance to Table 1, provided infra.

TABLE 1

Inhibitory Activity of Compounds

| Compounds: Example # | Human NEP $IC_{50}$ (nM) |
|---|---|
| Example 3-1 | 0.09 |
| Example 3-2 | 0.3 |
| Example 3-4 | 11 |
| Example 3-7 | 2.4 |
| Example 3-10 | 91 |
| Example 3-12 | 0.2 |
| Example 3-13 | 0.2 |

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula I', I, II, III or IV, or a pharmaceutically acceptable salt thereof, and at least one other therapeutic agent as a combined preparation for simultaneous, separate or sequential use in therapy. In one embodiment, the therapy is the treatment of a disease or condition associated with neutral endopeptidase EC 3.4. 24.11 activity.

Products provided as a combined preparation include a composition comprising the compound of formula I', I, II, III or IV, or a pharmaceutically acceptable salt thereof, and the other therapeutic agent(s) together in the same pharmaceutical composition, or the compound of formula I', I, II, III or IV, or a pharmaceutically acceptable salt thereof, and the other therapeutic agent(s) in separate form, e.g. in the form of a kit.

In one embodiment, the invention provides a pharmaceutical composition comprising a compound of formula I', I, II, III or IV, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula I', I, II, III or IV, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides the use of a compound of formula I', I, II, III or IV, or a pharmaceutically acceptable salt thereof, for treating a disease or condition associated with neutral endopeptidase EC 3.4. 24.11 activity, wherein the medicament is prepared for administration with another therapeutic agent. The invention also provides the use of another therapeutic agent for treating a disease or condition associated with neutral endopeptidase EC 3.4. 24.11 activity, wherein the medicament is administered with a compound of formula I', I, II, III or IV, or a pharmaceutically acceptable salt thereof.

The invention also provides a compound of formula I', I, Ill, III or IV, or a pharmaceutically acceptable salt thereof, for use in a method of treating a disease or condition associated with neutral endopeptidase EC 3.4. 24.11 activity, wherein the compound of formula I', I, II, III or IV, or a pharmaceutically acceptable salt thereof, is prepared for administration with another therapeutic agent. The invention also provides another therapeutic agent for use in a method of treating a disease or condition associated with neutral endopeptidase EC 3.4. 24.11 activity, wherein the other therapeutic agent is prepared for administration with a compound of formula I', I, II, III or IV, or a pharmaceutically acceptable salt thereof. The invention also provides a compound of formula I', I, II, III, or IV, or a pharmaceutically acceptable salt thereof, for use in a method of treating a disease or condition associated with neutral endopeptidase EC 3.4. 24.11 activity, wherein the compound of formula I', I, II, III or IV, or a pharmaceutically acceptable salt thereof, is administered with another therapeutic agent. The invention also provides another therapeutic agent for use in a method of treating a disease or condition associated with neutral endopeptidase EC 3.4. 24.11 activity, wherein the other therapeutic agent is administered with a compound of formula I', I, II, III or IV, or a pharmaceutically acceptable salt thereof.

The invention also provides the use of a compound of formula I', I, II, III or IV, or a pharmaceutically acceptable salt thereof, for treating a disease or condition associated with neutral endopeptidase EC 3.4. 24.11 activity, wherein the patient has previously (e.g. within 24 hours) been treated with another therapeutic agent. The invention also provides the use of another therapeutic agent for treating a disease or condition associated with neutral endopeptidase EC 3.4. 24.11 activity, wherein the patient has previously (e.g. within 24 hours) been treated with a compound of formula I', I, II, III or IV, or a pharmaceutically acceptable salt thereof.

In one embodiment, the other therapeutic agent is selected from:

In one embodiment, the other therapeutic agent is selected from: HMG-Co-A reductase inhibitor, an anigiotensin receptor blocker (ARBs, angiotensin II receptor antagonist), angiotensin converting enzyme (ACE) Inhibitor, a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors (ASI), a CETP inhibitor and a phophodiesterase type 5 (PDE5) inhibitor.

The term "in combination with" a second agent or treatment includes co-administration of the compound of the invention (e.g., a compound according to anyone of Formulae I-IV or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g. a disorder or disease responsive to the inhibition of neutral endopeptidase, such as for example, hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and atherosclerosis, male and female sexual dysfunction.

Examples of second agents include HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropy]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

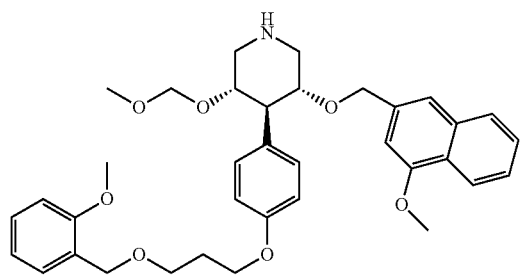

(A)

and

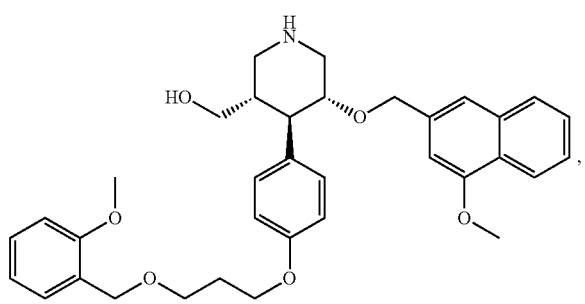

(B)

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

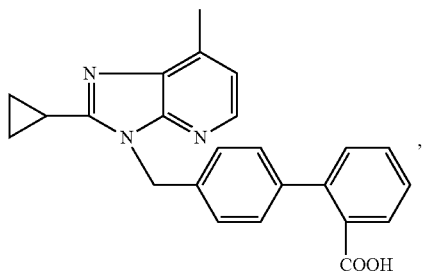 [SMILES: Cc1ccnc2c1nc(C1CC1)n2Cc1ccc(-c2ccccc2C(=O)O)cc1]

the compound with the designation SC-52458 of the following formula and the compound with the designation ZD-8731 of the following formula or, in each case, a pharmaceutically acceptable salt thereof.

Preferred $AT_1$-receptor antagonist are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

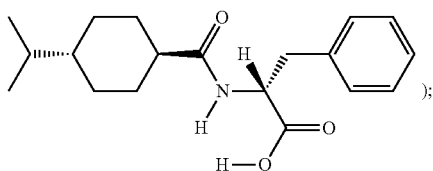 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia,* 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR8-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione(darglitazone), 5-{[4-(1-methyl-cyclohexyl)methoxy)-phenyl]methyl}-thiazolidine-2,4-dione(ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl)-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzylphiazolidine-2,4-dione (DN-108) 5-[4-(2-(2,3-dihydroindol-1-yl)ethoxy)phenyl] methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione(pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

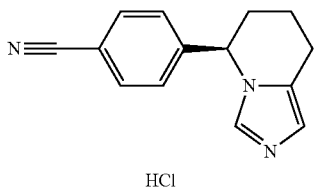 [SMILES: N#Cc1ccc([C@H]2CCCc3cncn32)cc1 ; Cl]

or, if appropriable, a pharmaceutically acceptable salt thereof.

A preferred steroidal aldosterone antagonist is eplerenone (cf. EP 122232 A) of the formula

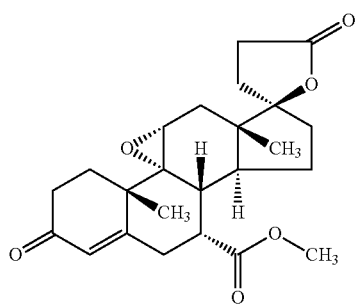

or Spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-dimidazol-5-yl)benzonitrile; cis-3-Fluoro-447-(4-fluoro-benzyl)-5,6,7,8-tetrahydro-imidazo[1,5-a]pyridin-5-yl)benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl) biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl1-5,6-dihydro-8H-imidazo[5,1-c][1,4]oxazine as developed by Speedel or in each case, the (R) or (S) enantiomer thereof; or if appropriable, a pharmaceutically acceptable salt thereof.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.;* 6:1951-1954 (1996), respectively. Furthermore, the CETP inhibitors also include those disclosed in WO2000/017165, WO2005/095409 and WO2005/097806.

A preferred PDE5 inhibitor is Sildenafil.

Second agent of particular interest include Endothelin antagonists, renin inhibitors, angiotensin II receptor antagonists, calcium channel blockers, diuretics, antidiabetic agents such as DPPIV inhibitors, and aldosterone synthase inhibitors.

In one embodiment, the invention provides a combination, in particular a pharmaceutical combination, comprising a therapeutically effective amount of the compound according to the definition of formula I', I, II, III or IV or a pharmaceutically acceptable salt thereof, and one or more therapeutically active agents selected from HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

In one embodiment, the invention provides a method of inhibiting neutral endopeptidase EC 3.4. 24.11 activity in a subject, wherein the method comprises administering to the subject a therapeutically effective amount of the compound according to the definition of formula I', I, II, III or IV or a pharmaceutically acceptable salt thereof.

In one embodiment, the invention provides a method of treating a disorder or a disease in a subject associated with neutral endopeptidase EC 3.4. 24.11 activity, wherein the method comprises administering to the subject a therapeutically effective amount of the compound according to the definition of formula I', I, II, III or IV or a pharmaceutically acceptable salt thereof.

In one embodiment, the invention provides a method of treating a disorder or a disease in a subject associated with neutral endopeptidase EC 3.4. 24.11 activity, wherein the disorder or the disease is selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retension), diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction.

In one embodiment, the invention provides a compound according to the definition of formula I', I, II, III or IV, for use as a medicament.

In one embodiment, the invention provides the use of a compound according to the definition of formula I', I, II, III or IV or a pharmaceutically acceptable salt thereof, for the treatment of a disorder or disease in a subject associated with neutral endopeptidase EC 3.4. 24.11 activity.

In one embodiment, the invention provides the use of a compound according to the definition of formula I', I, II, III or IV, in the manufacture of a medicament for the treatment of a disorder or disease in a subject characterized by an activity of neutral endopeptidase EC 3.4. 24.11, wherein said disorder or disease is in particular selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction.

In one embodiment, the invention provides the use of a compound according to the definition of formula I', I, II, III or IV, for the treatment of a disorder or disease in a subject characterized by an activity of neutral endopeptidase EC 3.4. 24.11, wherein the disorder or disease is selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency (diabetic or non-diabetic), renal failure (including edema and salt retention), diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction Exemplification of the Invention The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Exemplification of the Invention

Abbreviations:

| | |
|---|---|
| br: broad | bs: broad singlet |
| Ac: Acetyl | Atm: atmosphere |
| Aq: aqueous | calcd: calculated |
| Bn: benzyl | Boc: tert-butoxycarbonyl |
| d: doublet | dd: doublet of doublets |
| DCM: dichloromethane | DME: 1,4-dimethoxyethane |
| DMF: N,N-dimethylformamide | DMSO: dimethylsulfoxide |
| DAD: diode array detector | DTT: dithiothreitol |
| EDTA: ethylenediamine tetraacetic acid | ESI: electrospray ionization |
| Et and EtOAc: ethyl and ethyl acetate | |
| HATU: O-(7-azobenzotriazol-1-yl)-1,1,3,3-tetramethyluroniumhexafluorophosphate | HOBt: 1-hydroxy-7-azabenzotriazole |
| HPLC: high pressure liquid chromatography | LC and LCMS: liquid chromatography and liquid chromatography and mass spectrometry |
| HPLC-RT: high pressure liquid chromatography-retention time | |
| H: Hour(s) | IR: infrared |
| MeOH: methanol | MS: mass spectrometry |
| m: multiplet | min: minutes |
| Me: methyl | m/z: mass to charge ratio |
| M and mM: Molar and millimole(s) | Mg: milligram |
| n.d.: not determined | NMR: nuclear magnetic resonance |
| PMBCl: para-methoxybenzyl chloride | Pr and iPr: propyl and iso-propyl |
| ppm: parts per million | Pd/C: Palladium on Carbon |
| Ph: Phenyl | q: quartet |
| RP: reverse phase | RT: room temperature |
| s: singlet | t: triplet |
| TFA: trifluoroacetic acid | THF: tetrahydrofuran |
| TLC: thin layer chromatography | tBu: tert-butyl |
| μL, mL and L: microlitre, millilitre and litre | Tris•HCl: aminotris(hydroxymethyl)methane hydrochloride |
| wt: weight | UV: ultraviolet |

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The compounds in the examples 3-1 and 3-2 to 3-15 have been found to have $IC_{50}$ values in the range of about 0.001 nM to about 10,000 nM for NEP.

The conditions for measuring the retention times are as follows:

HPLC Condition A:

Column: INERTSIL C8-3, 3 μm×33 mm×3.0 mm at 40° C.

Flow rate: 2 mL/min

Mobile phase: A) 0.5 mM ammonium formate in $H_2O$; B) 50% MeOH in $CH_3CN$

Gradient: linear gradient from 5% B to 95% B in 2 min

Detection: DAD-UV at 210-400 nm

HPLC Condition B:

Column: 1NERTSIL C8-3, 3 μm×33 mm×3.0 mm at 40° C.

Flow rate: 2 mL/min

Mobile phase: A) 0.1% formic acid in $H_2O$; B) 50% MeOH in $CH_3CN$

Gradient: linear gradient from 5% B to 95% B in 2 min

Detection: DAD-UV at 210-400 nm

HPLC Condition C:

Column: INERTSIL C8-3, 3 μm×33 mm×3.0 mm at 40° C.

Flow rate: 2 mL/min

Mobile phase: A) 0.5 mM ammonium formate in $H_2O$; B) 50% MeOH in $CH_3CN$

Gradient: linear gradient from 40% B to 95% B in 2 min

Detection: DAD-UV at 210-400 nm

HPLC Condition D:

Column: INERTSIL C8-3, 3 μm×33 mm×3.0 mm at 40° C.

Flow rate: 2 mL/min

Mobile phase: A) 0.1% formic acid in $H_2O$; B) 50% MeOH in $CH_3CN$

Gradient: linear gradient from 40% B to 95% B in 2 min

Detection: DAD-UV at 210-400 nm

The relative stereochemistry was determined using two dimensional NMR. Under the reaction conditions, the racemization of the stereocenter bearing the bis-phenylmethyl group is not expected. Therefore the absolute stereochemistry was determined based on the relative stereochemistry and the stereochemistry of the center bearing the bisphenylmethyl group.

Example 1-1

Synthesis of (S)-2-[(S)-2-(3'-chloro-biphenyl-4-yl)-1-(1H-tetrazol-5-ylcarbamoyl)-ethylamino]-propionic acid ethyl ester

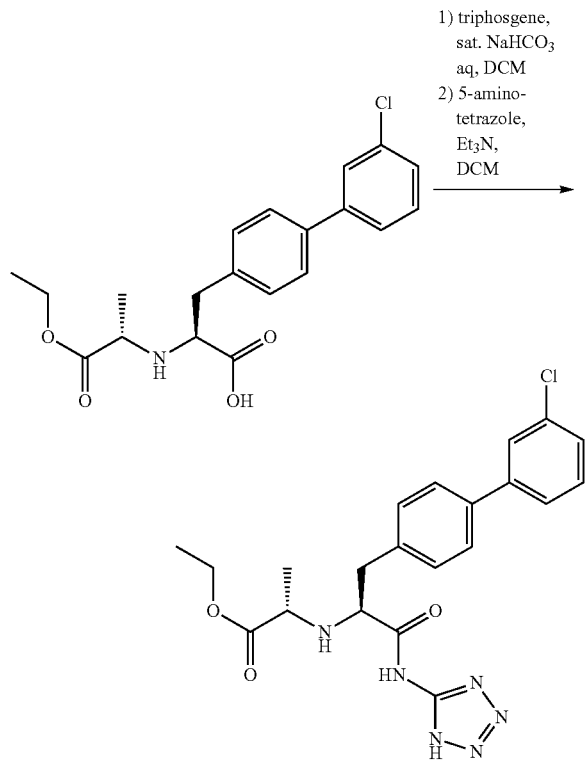

1) triphosgene, sat. NaHCO₃ aq, DCM
2) 5-amino-tetrazole, Et₃N, DCM

To a suspension of (S)-3-(3'-chloro-biphenyl-4-yl)-2-((S)-1-ethoxycarbonyl-ethylamino)-propionic acid (4.0 g, 10.84 mmol) in dichloromethane (60 mL) and saturated aqueous NaHCO₃ (10 mL) was added triphosgene (1.90 g, 6.39 mmol). After vigorously stirred for 0.5 hour, the reaction mixture was diluted with EtOAc and partially concentrated under reduced pressure. Excess of triphosgene was quenched by adding saturated aqueous NaHCO₃ and stirred for 0.5 hour. The mixture was extracted with EtOAc and washed with brine. The organic layer was dried over Na₂SO₄ and concentrated under reduced pressure. The obtained residue was dissolved in dichloromethane (50 mL). To the mixture was added triethylamine (1.93 mL, 13.8 mmol) and 5-amino-1H-tetrazole (1.18 g, 13.84 mmol) at 0° C., and the reaction mixture was gradually warmed to room temperature. After stirred for 2 hours, the reaction mixture was concentrated and purified by silica gel column chromatography (eluent: 10% MeOH in dichloromethane) to give a mixture of the desired trans isomer product and the cis isomer. The obtained material was re-crystallized from CH₃CN three times to give (S)-2-[(S)-2-(3'-chloro-biphenyl-4-yl)-1-(1H-tetrazol-5-ylcarbamoyl)-ethylamino]-propionic acid ethyl ester (3.92 g). $^1$H NMR (400 MHz, DMSO-d6) δ 1.11 (t, 3H, J=7.1 Hz), 1.15 (d, 3H, J=6.8 Hz), 2.89 (dd, 1H, J=8.1, 13.7 Hz), 3.02 (dd, 1H, J=5.8, 14.0 Hz), 3.27-3.36 (m, 1H), 3.75-3.83 (m, 1H), 4.01 (q, 2H, J=7.1 Hz), 7.34 (d, 2H, J=8.3 Hz), 7.38-7.42 (m, 1H), 7.47 (dd, 1H, J=7.8, 7.8 Hz), 7.60-7.65 (m, 3H), 7.69 (dd, 1H, J=1.8, 1.8 Hz); MS: m/z (MH⁺) 443; HRMS: calculated for C₂₂H₂₃ClN₆O₃ (M)⁺ 442.1, found 442.1; EA: Calculated for C21H23ClN6O3: C, 56.95; H, 5.23; N, 18.97. Found: C, 56.88; H, 5.07; N, 19.1.

Chiral HPLC retention time=9.26 min. [condition: Daicel CHIRALCEL OJ-H 4.6×100 mm); flow rate=1 ml/min.; eluent: 20% EtOH (with 0.1% TFA) in heptane].

Following compounds were prepared using similar procedure as example 1-1 with appropriate intermediates:

| Example # | Product | Intermediates | HPLC-RT (condition) | MS (M + 1) |
|---|---|---|---|---|
| Example 1-2 | (S)-2-[(S)-2-(2',5'-Dichloro-biphenyl-4-yl)-1-(1H-tetrazol-5-ylcarbamoyl)-ethylamino]-propionic acid tert-butyl ester | (S)-2-((S)-1-tert-Butoxycarbonyl-ethylamino)-3-(2',5'-dichloro-biphenyl-4-yl)-propionic acid And 5-amino-1H-tetrazole | 1.38 min (C) | 505 |

-continued

| Example # | Product | Intermediates | HPLC-RT (condition) | MS (M + 1) |
|---|---|---|---|---|
| Example 1-3 | 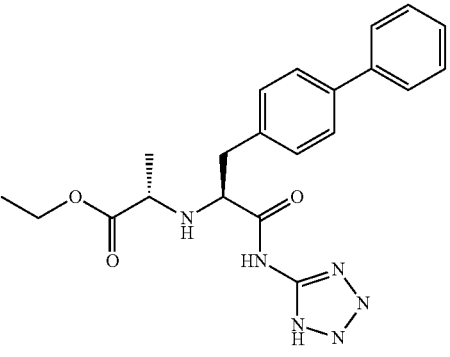<br>(S)-2-[(S)-2-Biphenyl-4-yl-1-(1H-tetrazol-5-ylcarbamoyl)-ethylamino]-propionic acid ethyl ester | 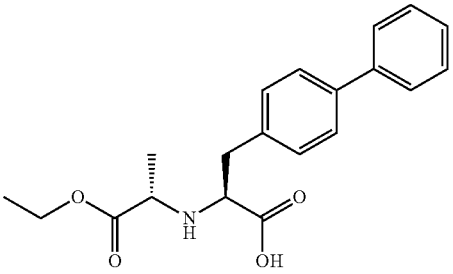<br>(S)-3-Biphenyl-4-yl-2-((S)-1-ethoxy-carbonyl-ethylamino)-propionic acid<br>And<br>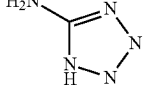<br>5-amino-1H-tetrazole | 1.55 min (A) | 409 |
| Example 1-4 | 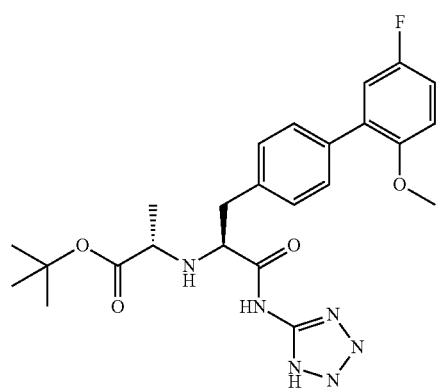<br>(S)-2-[(S)-2-(5'-Fluoro-2'-methoxy-biphenyl-4-yl)-1-(1H-tetrazol-5-yl-carbamoyl)-ethylamino]-propionic acid tert-butyl ester | 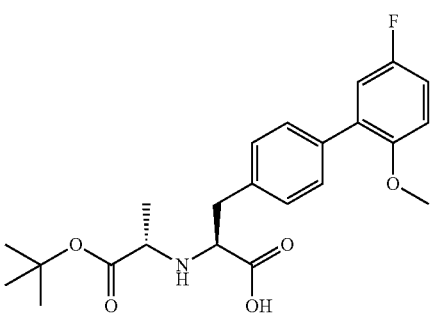<br>(S)-2-((S)-1-tert-Butoxycarbonyl-ethylamino)-3-(5'-fluoro-2'-methoxy-biphenyl-4-yl)-propionic acid<br>And<br>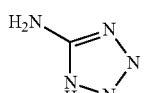<br>5-amino-1H-tetrazole | 1.27 min (C) | 485 |

-continued

| Example # | Product | Intermediates | HPLC-RT (condition) | MS (M + 1) |
|---|---|---|---|---|
| Example 1-5 | 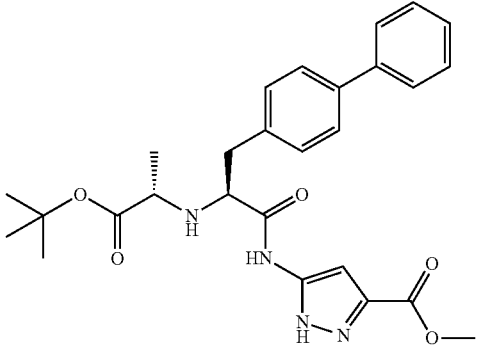 5-[(S)-3-Biphenyl-4-yl-2-((S)-1-tert-butoxycarbonyl-ethylamino)-propionylamino]-1H-pyrazole-3-carboxylic acid methyl ester | 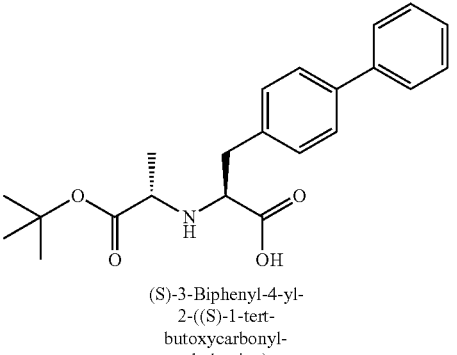 (S)-3-Biphenyl-4-yl-2-((S)-1-tert-butoxycarbonyl-ethylamino)-propionic acid And 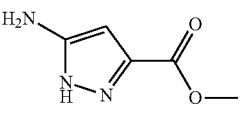 5-amino-1H-pyrazole-3-carboxylic acid methyl ester | 1.49 min (C) | 493 |
| Example 1-6 | 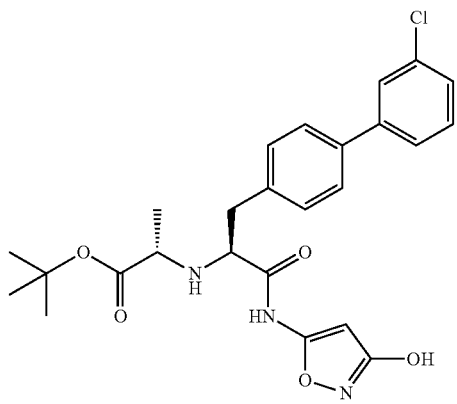 (S)-2-[(S)-2-(3'-Chloro-biphenyl-4-yl)-1-(3-hydroxy-isoxazol-5-ylcarbamoyl)-ethylamino]-propionic acid tert-butyl ester | 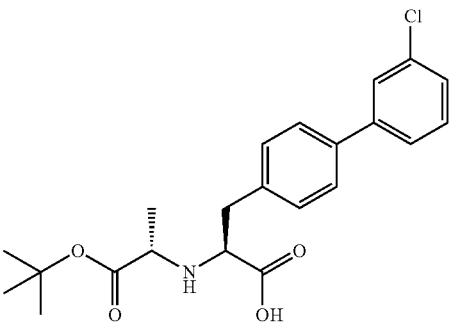 (S)-2-((S)-1-tert-Butoxycarbonyl-ethylamino)-3-(3'-chloro-biphenyl-4-yl)-propionic acid And 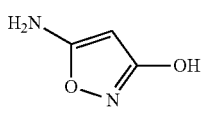 5-amino-isoxazole-3-ol | 1.48 min (C) | 486 |

| Example # | Product | Intermediates | HPLC-RT (condition) | MS (M + 1) |
|---|---|---|---|---|
| Example 1-7 | 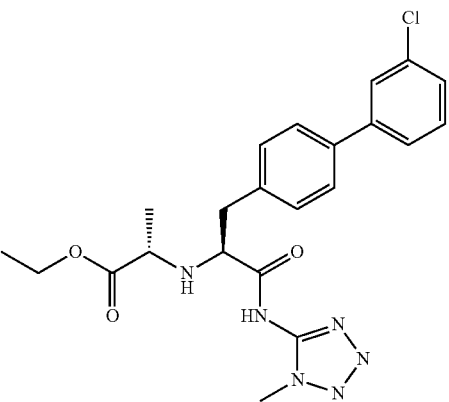<br>(S)-2-[(S)-2-(3'-Chloro-biphenyl-4-yl)-1-(1-methyl-1H-tetrazol-5-ylcarbamoyl)-ethylamino]-propionic acid ethyl ester | 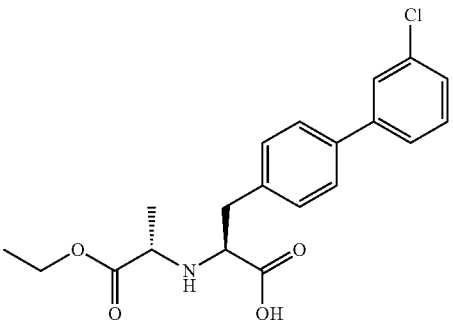<br>(S)-3-(3'-Chloro-biphenyl-4-yl)-2-((S)-1-ethoxycarbonyl-ethylamino)-propionic acid<br>And<br>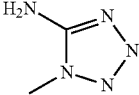<br>1-methyl-1H-tetrazol-5-ylamine | 1.12 min (C) | 457 |
| Example 1-8 | 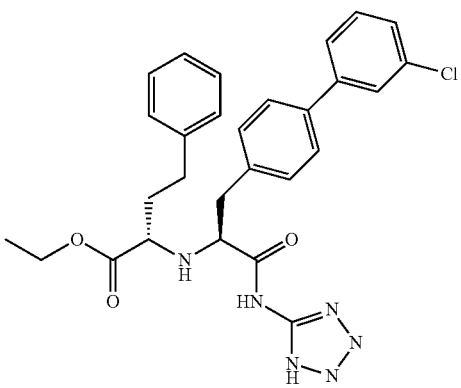<br>(S)-2-[(S)-2-(3'-Chloro-biphenyl-4-yl)-1-(1H-tetrazol-5-ylcarbamoyl)-ethylamino]-4-phenyl-butyric acid ethyl ester | 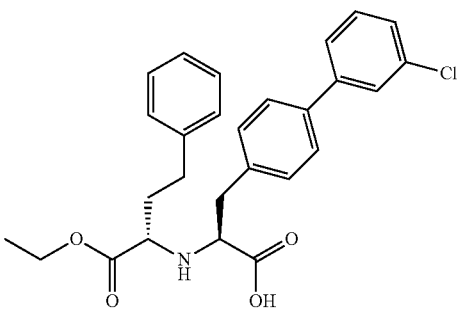<br>(S)-2-[(S)-1-carboxy-2-(3'-chloro-biphenyl-4-yl)-ethylamino]-4-phenyl-butyric acid ethyl ester<br>And<br>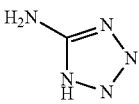<br>5-amino-1H-tetrazole | 1.47 min. (C) | 533.4 |

-continued

| Example # | Product | Intermediates | HPLC-RT (condition) | MS (M + 1) |
|---|---|---|---|---|
| Example 1-9 | 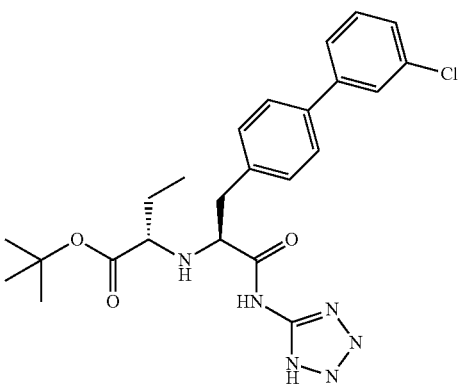<br>(S)-2-[(S)-2-(3'-Chloro-biphenyl-4-yl)-1-(1H-tetrazol-5-ylcarbamoyl)-ethylamino]-butyric acid tert-butyl ester | 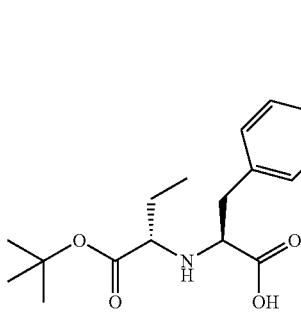<br>(S)-2-[(S)-1-Carboxy-2-(3'-chloro-biphenyl-4-yl)-ethylamino]-butyric acid tert-butyl ester<br>And<br>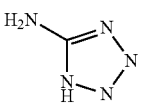<br>5-amino-1H-tetrazole | 1.27 (C) | 485 |
| Example 1-10 | 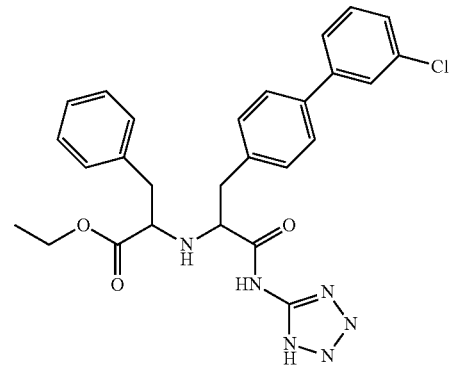<br>2-[2-(3'-Chloro-biphenyl-4-yl)-1-(1H-tetrazol-5-ylcarbamoyl)-ethylamino]-3-phenyl-propionic acid ethyl ester | 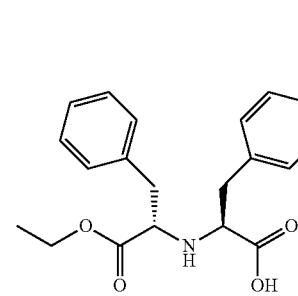<br>(S)-3-(3'-Chloro-biphenyl-4-yl)-2-((S)-1-ethoxycarbonyl-2-phenyl-ethyl-amino)-propionic acid<br>And<br>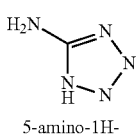<br>5-amino-1H-tetrazole | 1.31 (C) | 519 |

Experiment 1-11

(S)-2-{(S)-2-(3'-chloro-biphenyl-4-yl)-1-[methyl-(1H-tetrazol-5-yl)-carbamoyl]-ethylamino}-propionic acid ethyl ester

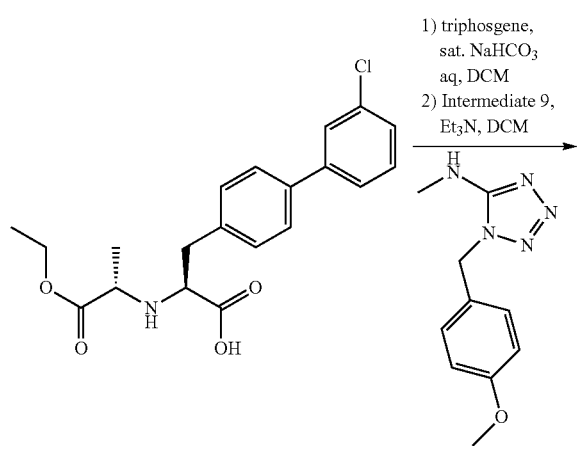

Intermediate 9

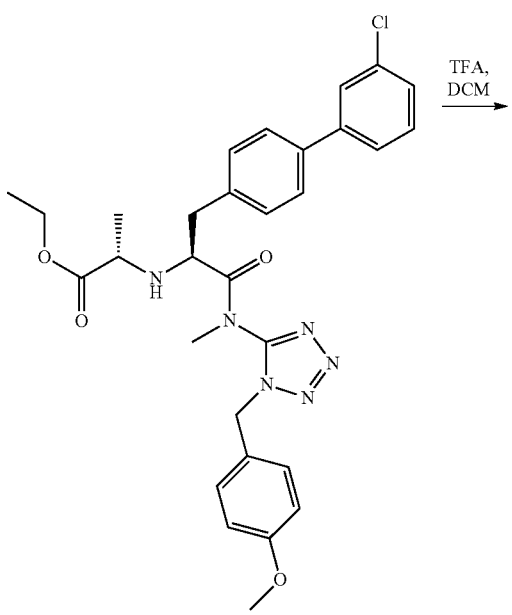

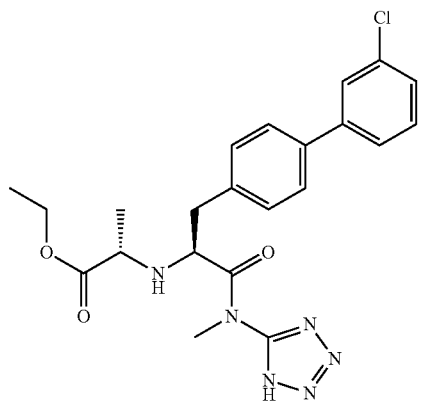

To a suspension of (S)-3-(3'-chloro-biphenyl-4-yl)-2-((S)-1-ethoxycarbonyl-ethylamino)-propionic acid (225 mg, 0.599 mmol) in dichloromethane (4 mL) and saturated aqueous $NaHCO_3$ (1 mL) was added triphosgene (178 mg, 0.599 mmol). After vigorously stirred for 10 min, the reaction mixture was diluted with EtOAc and partially concentrated under reduced pressure. Excess of triphosgene was quenched by adding saturated aqueous $NaHCO_3$ and stirred for 0.5 hour. The mixture was extracted with EtOAc and washed with brine. The organic layer was dried over $Na_2SO_4$ and concentrated under reduced pressure. The obtained residue was dissolved in dichloromethane (5 mL). To the mixture were added triethylamine (0.167 mL, 1.197 mmol) and [1-(4-methoxy-benzyl)-1H-tetrazol-5-yl]-methyl-amine (197 mg, 0.898 mmol) and stirred at 45° C. overnight. Additional triethylamine (0.167 mL, 1.197 mmol) and [1-(4-methoxy-benzyl)-1H-tetrazol-5-yl]-methyl-amine (197 mg, 0.898 mmol) were added and stirred at 45° C. for 30 hours. The reaction mixture was concentrated under reduced pressure and purified by silica gel column chromatography (eluent: 10% MeOH in DCM) to give (S)-2-((S)-2-(3'-chloro-biphenyl-4-yl)-1-{[1-(4-methoxy-benzyl)-1H-tetrazol-5-yl]-methyl-carbamoyly-ethylamino)-propionic acid ethyl ester (261 mg). MS: m/z (MH$^+$) 577; HPLC retention time 1.36 min (HPLC condition C).

Next, (S)-2-((S)-2-(3'-chloro-biphenyl-4-yl)-1-{[1-(4-methoxy-benzyl)-1H-tetrazol-5-yl]-methyl-carbamoyl}-ethylamino)-propionic acid ethyl ester (260 mg, 0.451 mmol) was dissolved in TFA (5 mL) and DCM (5 mL) and stirred at 50° C. for 12 hours and at 75° C. for 5 hours. The reaction mixture was concentrated under reduced pressure to give (S)-2-{(S)-2-(3'-chloro-biphenyl-4-yl)-1-[methyl-(1H-tetrazol-5-yl)-carbamoyl]-ethylamino}-propionic acid ethyl ester (120 mg). MS: m/z (MH$^+$) 457; HPLC retention time 0.95 min (HPLC condition C).

Following compounds were prepared using similar procedure as example 1-1 with appropriate intermediates:

| Example # | Product | Intermediates | HPLC-RT (condition) | MS (M + 1) |
|---|---|---|---|---|
| Example 1-12 | 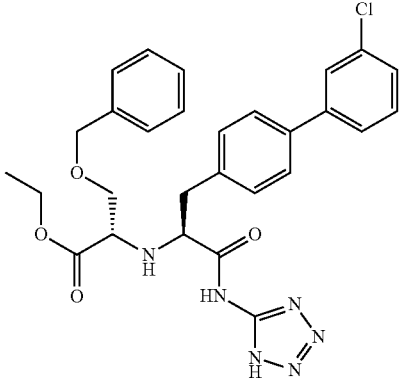<br>(S)-3-benzyloxy-2-[(S)-2-(3'-chloro-biphenyl-4-yl)-1-(1H-tetrazol-5-ylcarbamoyl)-ethylamino]-propionic acid ethyl ester | 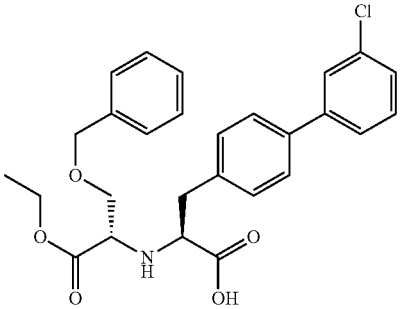<br>(S)-2-((S)-2-benzyloxy-1-ethoxycarbonyl-ethylamino)-3-(3'-chloro-biphenyl-4-yl)-propionic acid<br>And<br>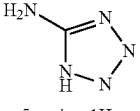<br>5-amino-1H-tetrazole | 1.31 min (C) | 549 |
| Example 1-13 | 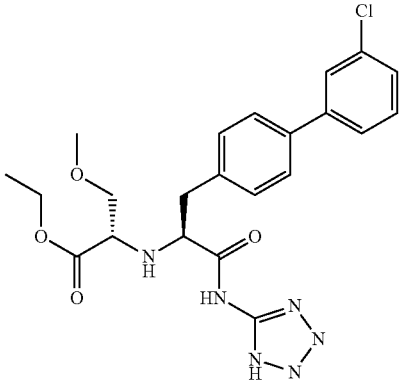<br>(S)-2-[(S)-2-(3'-chloro-biphenyl-4-yl)-1-(1H-tetrazol-5-ylcarbamoyl)-ethylamino]-3-methoxy-propionic acid ethyl ester | 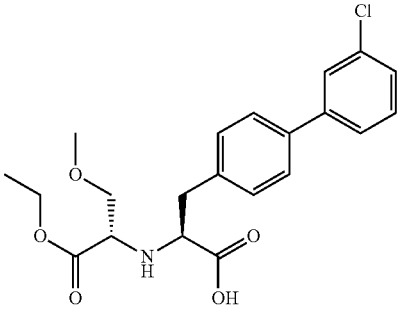<br>(S)-3-(3'-chloro-biphenyl-4-yl)-2-((S)-1-ethoxycarbonyl-2-methoxy-ethylamino)-propionic acid<br>And<br>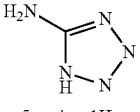<br>5-amino-1H-tetrazole | 1.29 min (A) | 471 |

Example 1-14

(S)-2-[(S)-2-(3'-chloro-biphenyl-4-yl)-1-(1H-tetrazol-5-ylcarbamoyl)-ethoxy]-propionic acid ethyl ester

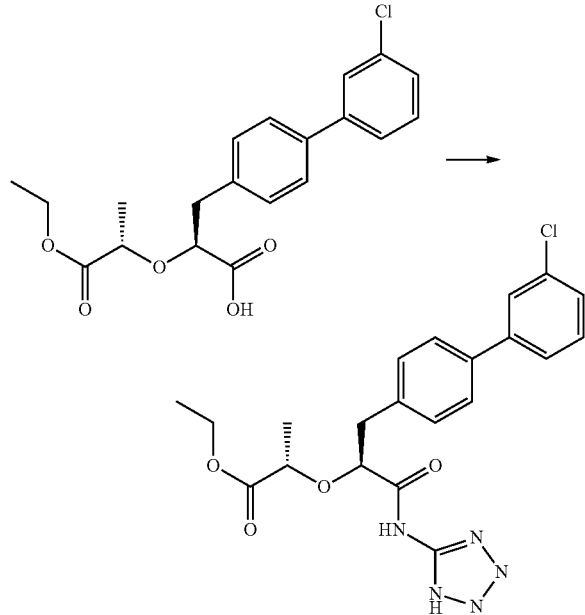

To a solution of (S)-3-(3'-chloro-biphenyl-4-yl)-2-((S)-1-ethoxycarbonyl-ethoxy)-propionic acid (62 mg, 0.165 mmol) in THF (5 ml) at room temperature was added 5-aminotetrazole (38.0 mg, 0.447 mmol), DIPEA (0.086 ml, 0.494 mmol) and followed by 1,3-diisopropylcarbodiimide (0.060 ml, 0.387 mmol). The reaction was stirred at room temperature for 3 hr. The reaction was quenched by brine and was extracted with EtOAc. The combined organic layer was washed with brine and dried over anhydrous sodium sulfate, filtered and concentrated. HPLC retention time=0.99 minutes (condition C); MS (m+1)=444.

Example 2-1

(S)-2-[(R)-2-(3'-chloro-biphenyl-4-yl)-1-(1H-tetrazol-5-ylcarbamoyl)-ethylamino]-propionic acid ethyl ester

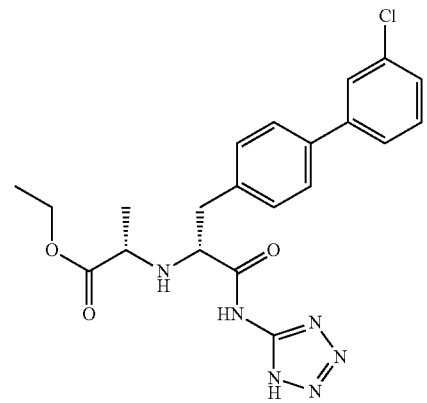 [SMILES: CCOC(=O)[C@H](C)N[C@H](Cc1ccc(-c2cccc(Cl)c2)cc1)C(=O)Nc1nnn[nH]1]

The cis isomer obtained from procedure described in Example 1-1 was isolated by reverse phase HPLC (Sunfire C-18 column, 0.1% TFA in $H_2O/CH_3CN$) to provide (S)-2-[(R)-2-(3'-chloro-biphenyl-4-yl)-1-(1H-tetrazol-5-ylcarbamoyl)-ethylamino]-propionic acid ethyl ester; $^1H$ NMR (400 MHz, DMSO-d6) δ 1.07 (t, 3H, J=7.1 Hz), 1.12 (d, 3H, J=6.8 Hz), 2.88 (dd, 1H, J=8.1, 13.6 Hz), 3.04 (dd, 1H, J=6.1, 13.6 Hz), 3.18-3.26 (m, 1H), 3.69-3.78 (m, 1H), 3.87-4.03 (m, 2H), 7.35 (d, 2H, J=8.1 Hz), 7.37-7.42 (m, 1H), 7.47 (dd, 1H, J=7.8, 7.8 Hz), 7.58-7.65 (m, 3H), 7.68-7.72 (m, 1H); MS: m/z (MH$^+$) 443.

Following compounds were prepared using similar procedure as example 1-1 and 2-1 with appropriate intermediates:

| Example # | Product | Intermediates | HPLC-RT (condition) | MS (M + 1) |
|---|---|---|---|---|
| Example 2-2 | (S)-2-[(R)-2-(2',5'-Dichloro-biphenyl-4-yl)-1-(1H-tetrazol-5-ylcarbamoyl)-ethylamino]-propionic acid tert-butyl ester | (S)-2-((S)-1-tert-Butoxycarbonyl-ethylamino)-3-(2',5'-dichloro-biphenyl-4-yl)-propionic acid And 5-amino-1H-tetrazole | 1.38 min (C) | 505 |

-continued

| Example # | Product | Intermediates | HPLC-RT (condition) | MS (M + 1) |
|---|---|---|---|---|
| Example 2-3 | 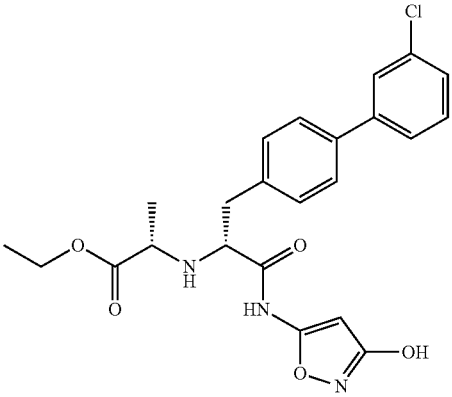<br>(S)-2-[(R)-2-(3'-Chloro-biphenyl-4-yl)-1-(3-hydroxy-isoxazol-5-ylcarbamoyl)-ethylamino]-propionic acid ethyl ester | 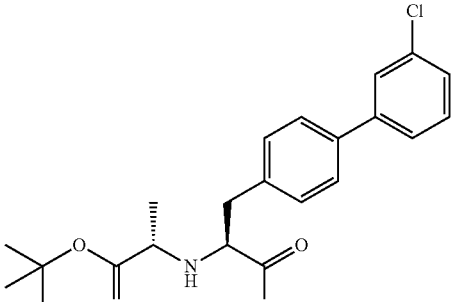<br>(S)-2-((S)-1-tert-Butoxycarbonyl-ethylamino)-3-(3'-chloro-biphenyl-4-yl)-propionic acid<br>And<br>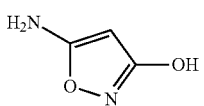<br>5-amino-isoxazole-3-ol | 1.46 min (C) | 486 |
| Example 2-4 | 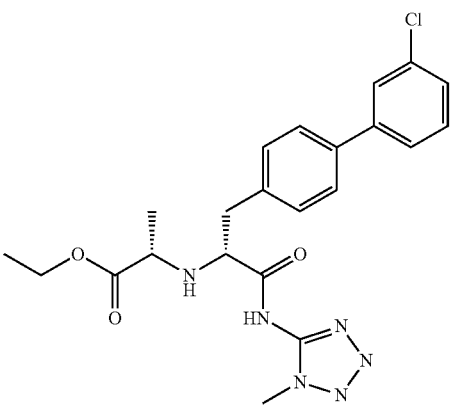<br>(S)-2-[(R)-2-(3'-Chloro-biphenyl-4-yl)-1-(1-methyl-1H-tetrazol-5-ylcarbamoyl)-ethylamino]-propionic acid ethyl ester | 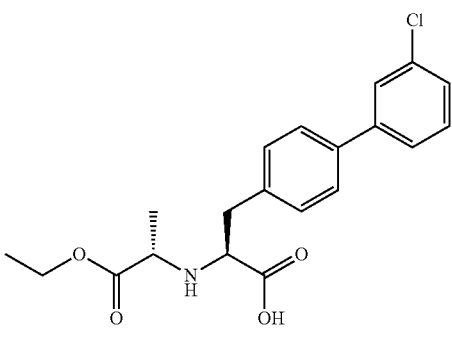<br>(S)-3-(3'-Chloro-biphenyl-4-yl)-2-((S)-1-ethoxycarbonyl-ethylamino)-propionic acid<br>And<br>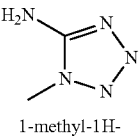<br>1-methyl-1H-tetrazol-5-ylamine | 1.16 min (C) | 457 |

Example 3-1

(S)-2-[(S)-2-(3'-chloro-biphenyl-4-yl)-1-(1H-tetrazol-5-ylcarbamoyl)-ethylamino]-propionic acid

Example 3-2

(S)-2-[(S)-2-(2',5'-dichloro-biphenyl-4-yl)-1-(1H-tetrazol-5-ylcarbamoyl)-ethylamino]-propionic acid

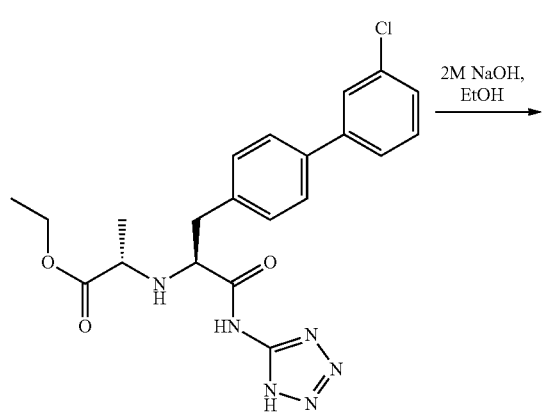

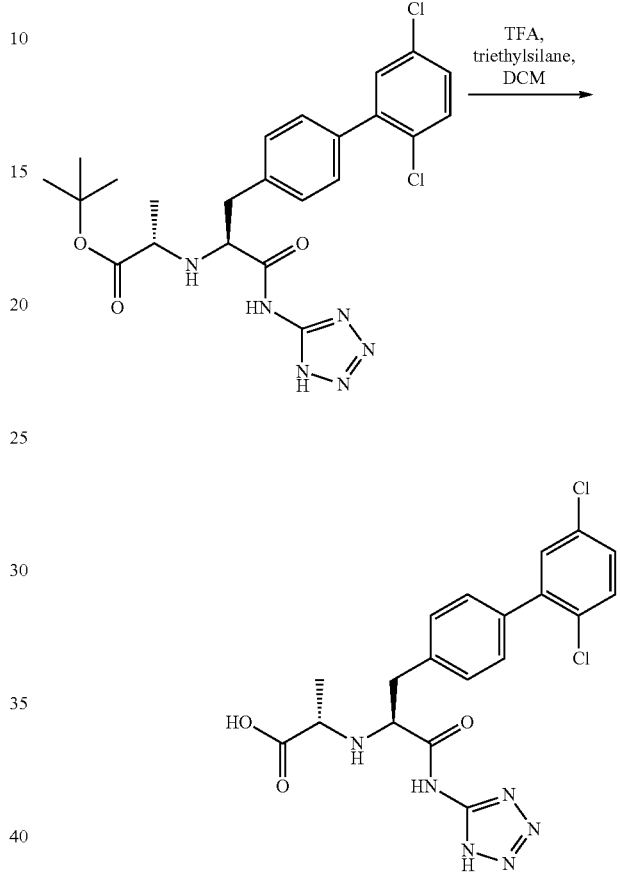

(S)-2-[(S)-2-(3'-chloro-biphenyl-4-yl)-1-(1H-tetrazol-5-ylcarbamoyl)-ethylamino]-propionic acid ethyl ester (100 mg, 0.226 mmol) was treated with 2M aqueous NaOH (2 mL) and EtOH (0.5 mL). After stirred at room temperature for 1 hour, the reaction mixture was acidified with 2M HCl to adjust pH 1. The resulted precipitate was collected by filtration. The obtained material was crystallized from EtOH to give (S)-2-[(S)-2-(3'-chloro-biphenyl-4-yl)-1-(1H-tetrazol-5-ylcarbamoyl)-ethylamino]-propionic acid (94 mg).

$^1$H NMR (400 MHz, DMSO-d6) δ 1.15 (d, 3H, J=7.1 Hz), 2.94 (dd, 1H, J=7.3, 13.7 Hz), 3.03 (dd, 1H, J=6.3, 13.6 Hz), 3.26 (dd, 1H, J=7.1, 13.9 Hz), 3.81 (dd, 1H, J=6.9, 6.9 Hz), 7.33 (d, 2H, J=8.3 Hz), 7.38-7.42 (m, 1H), 7.47 (dd, 1H, J=7.8, 7.8 Hz), 7.59-7.64 (m, 3H), 7.69 (dd, 1H, J=1.8, 1.8 Hz), 15.9 (bs, 1H); MS: m/z (MH$^+$) 415; HRMS: calculated for $C_{19}H_{19}ClN_6O_3$ (M)$^+$ 414.1, found 414.1

Chiral HPLC retention time=13.17 min. [condition: Daicel CHIRALPAK IA 4.6×100 mm); flow rate=1 ml/min.; eluent: 20% EtOH (with 0.1% TFA) in heptane].

To a solution of (S)-2-[(S)-2-(2',5'-dichloro-biphenyl-4-yl)-1-(1H-tetrazol-5-ylcarbamoyl)-ethylamino]-propionicacid tert-butyl ester (103 mg, 0.204 mmol) in DCM (2 mL) were added TFA (1 mL) and triethylsilane (0.098 mL, 0.611 mmol). After stirred for 8 hours, the reaction mixture was concentrated under reduced pressure. The residue was purified by reverse phase HPLC (Sunfire C-18 column, eluent: 0.1% TFA in H$_2$O/CH3CN) to give (S)-2-[(S)-2-(2',5'-dichloro-biphenyl-4-yl)-1-(1H-tetrazol-5-ylcarbamoyl)-ethylamino]-propionic acid. $^1$H NMR (400 MHz, DMSO-d6+TFA-d) δ 1.49 (d, 3H, J=7.1 Hz), 3.29 (dd, 1H, J=7.6, 13.9 Hz), 3.42 (dd, 1H, J=7.1, 14.2 Hz), 4.13 (dd, 1H, J=7.1, 14.0 Hz), 4.62 (dd, 1H, J=7.3, 7.3 Hz), 7.37 (d, 1H, J=2.5 Hz), 7.37-7.43 (m, 2H), 7.40 (d, 2H, J=4.3 Hz), 7.48 (dd, 1H, J=2.5, 8.6 Hz), 7.59 (d, 1H, J=8.6 Hz), 14.89 (bs, 1H); HPLC Retention time 1.25 minutes (condition A); MS: m/z (MH$^+$) 449.

Following compounds were prepared using similar procedure as example 3-1 or 3-2 with appropriate starting material and conditions:

| Example # | Product | Starting Material | Hydrolysis Condition | HPLC-RT (condition) | MS (M+1) |
|---|---|---|---|---|---|
| Example 3-3 | 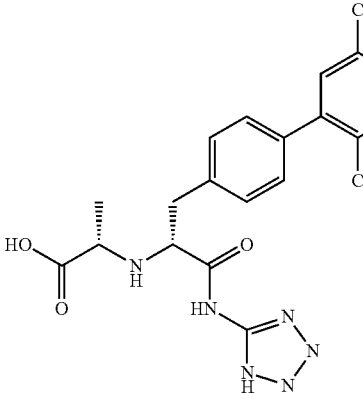<br>(S)-2-[(R)-2-(2′,5′-Dichloro-biphenyl-4-yl)-1-(1H-tetrazol-5-ylcarbamoyl)-ethylamino]-propionic acid | 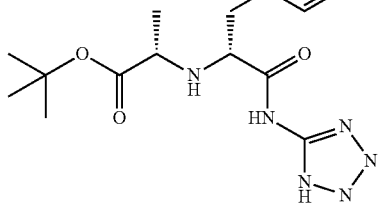<br>(S)-2-[(R)-2-(2′,5′-Dichloro-biphenyl-4-yl)-1-(1H-tetrazol-5-ylcarbamoyl)-ethylamino]-propionic acid tert-butyl ester | TFA, triethylsilane, DCM, RT | 1.30 min. (A) | 449 |
| Example 3-4 | 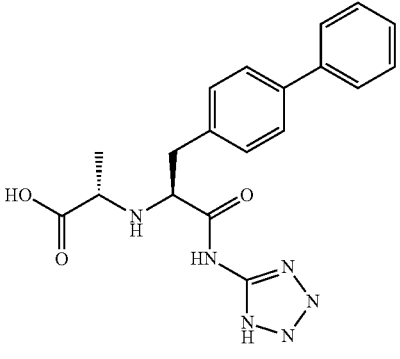<br>(S)-2-[(S)-2-Biphenyl-4-yl-1-(1H-tetrazol-5-ylcarbamoyl)-ethylamino]-propionic acid | 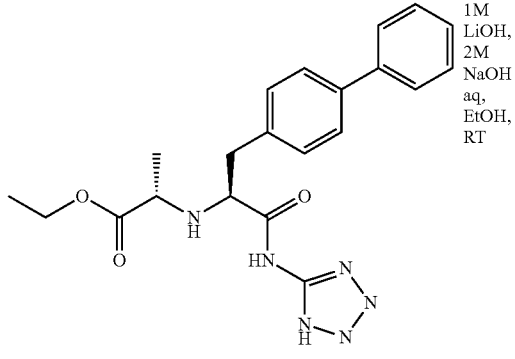<br>(S)-2-[(S)-2-Biphenyl-4-yl-1-(1H-tetrazol-5-ylcarbamoyl)-ethylamino]-propionic acid ethyl ester | 1M LiOH, 2M NaOH aq, EtOH, RT | 1.28 min. (B) | 381 |

-continued

| Example # | Product | Starting Material | Hydrolysis Condition | HPLC-RT (condition) | MS (M + 1) |
|---|---|---|---|---|---|
| Example 3-5 | 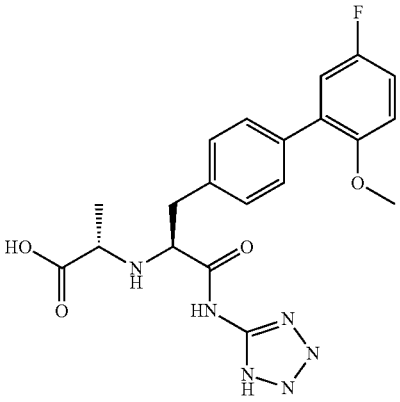<br>(S)-2-[(S)-2-(5′-Fluoro-2′-methoxy-biphenyl-4-yl)-1-(1H-tetrazol-5-ylcarbamoyl)-ethylamino]-propionic acid | 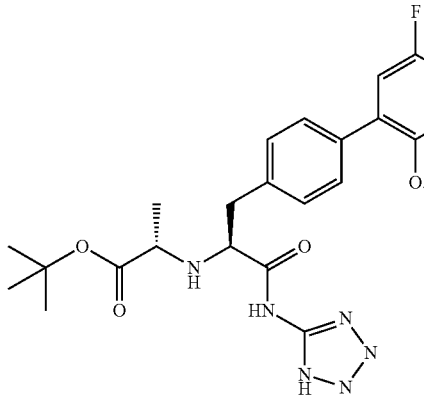<br>(S)-2-[(S)-2-(5′-Fluoro-2′-methoxy-biphenyl-4-yl)-1-(1H-tetrazol-5-yl-carbamoyl)-ethylamino]-propionic acid tert-butyl ester | TFA, triethyl-silane, DCM, RT | 1.19 min. (A) | 429 |
| Example 3-6 | 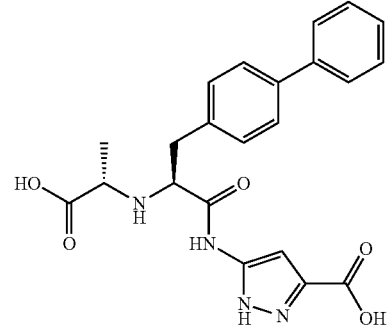<br>5-[(S)-3-Biphenyl-4-yl-2-((S)-1-carboxy-ethylamino)-propionylamino]-1H-pyrazole-3-carboxylic acid | 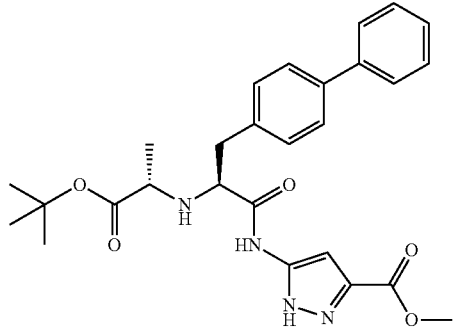<br>5-[(S)-3-Biphenyl-4-yl-2-((S)-1-tert-butoxycarbonyl-ethylamino)-propionylamino]-1H-pyrazole-3-carboxylic acid methyl ester | 2M NaOH aq, EtOH RT. Followed by TFA, DCM, RT | 1.26 min. (B) | 423 |

-continued

| Example # | Product | Starting Material | Hydrolysis Condition | HPLC-RT (condition) | MS (M + 1) |
|---|---|---|---|---|---|
| Example 3-7 | 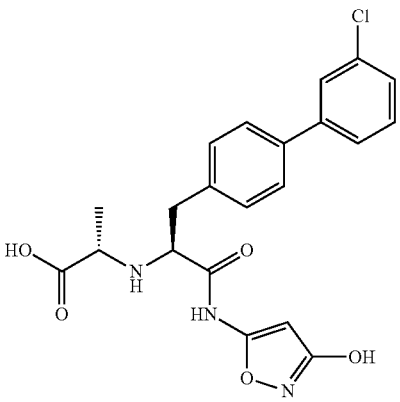 (S)-2-[(S)-2-(3'-Chloro-biphenyl-4-yl)-1-(3-hydroxy-isoxazol-5-ylcarbamoyl)-ethylamino]-propionic acid | 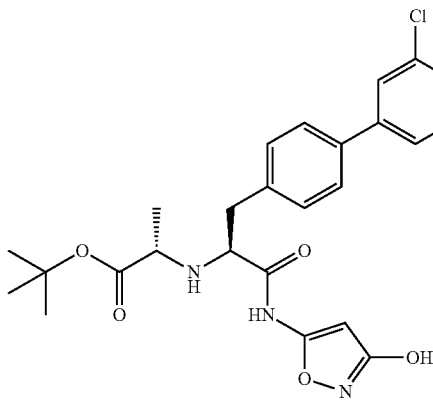 (S)-2-[(S)-2-(3'-Chloro-biphenyl-4-yl)-1-(3-hydroxy-isoxazol-5-ylcarbamoyl)-ethylamino]-propionic acid tert-butyl ester | TFA, triethylsilane, DCM, RT | 1.30 min. (A) | 430 |
| Example 3-8 | 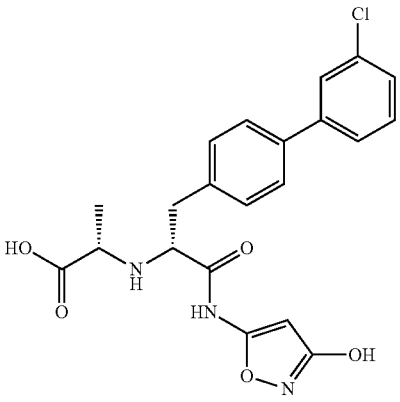 (S)-2-[(R)-2-(3'-Chloro-biphenyl-4-yl)-1-(3-hydroxy-isoxazol-5-ylcarbamoyl)-ethylamino]-propionic acid | 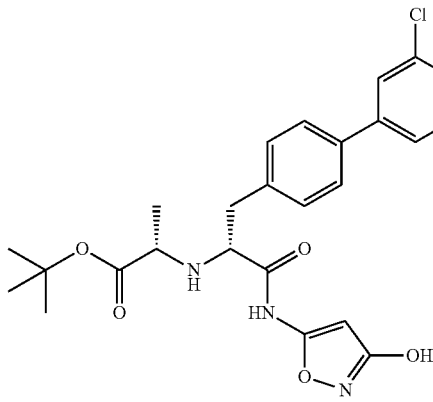 (S)-2-[(R)-2-(3'-Chloro-biphenyl-4-yl)-1-(3-hydroxy-isoxazol-5-ylcarbamoyl)-ethylamino]-propionic acid tert-butyl ester | TFA, triethylsilane, DCM, RT | 1.40 min. (A) | 430 |

-continued

| Example # | Product | Starting Material | Hydrolysis Condition | HPLC-RT (condition) | MS (M + 1) |
|---|---|---|---|---|---|
| Example 3-9 | 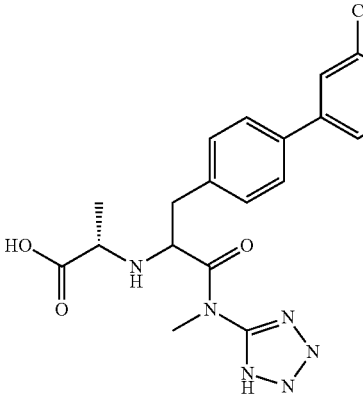<br>(S)-2-{2-(3'-Chloro-biphenyl-4-yl)-1-[methyl-(1H-tetrazol-5-yl)-carbamoyl]-ethylamino}-propionic acid | 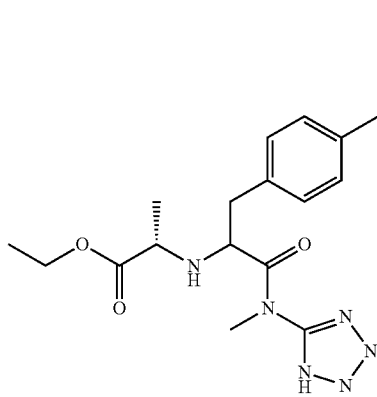<br>(S)-2-{2-(3'-Chloro-biphenyl-4-yl)-1-[methyl-(1H-tetrazol-5-yl)-carbamoyl]-ethylamino}-propionic acid ethyl ester | 2M NaOH aq, EtOH, RT | 1.16 min. (A) | 429 |
| Example 3-10 | 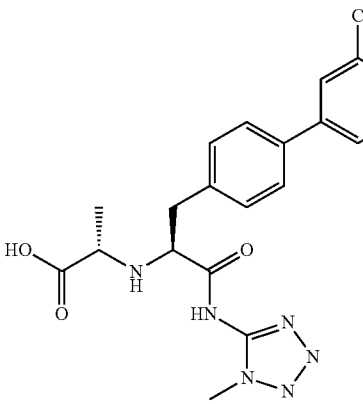<br>(S)-2-[(S)-2-(3'-Chloro-biphenyl-4-yl)-1-(1-methyl-1H-tetrazol-5-ylcarbamoyl)-ethylamino]-propionic acid | 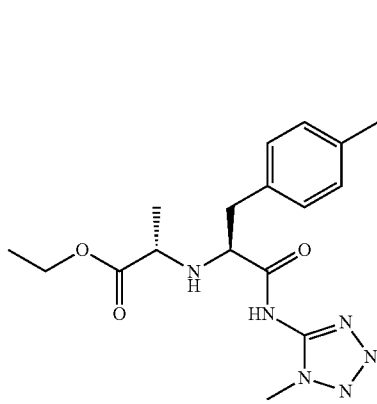<br>(S)-2-[(S)-2-(3'-Chloro-biphenyl-4-yl)-1-(1-methyl-1H-tetrazol-5-ylcarbamoyl)-ethylamino]-propionic acid ethyl ester | 2M NaOH aq, EtOH, RT | 1.38 min. (A) | 429 |

| Example # | Product | Starting Material | Hydrolysis Condition | HPLC-RT (condition) | MS (M+1) |
|---|---|---|---|---|---|
| Example 3-11 | 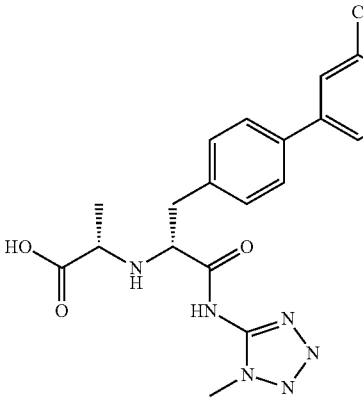<br>(S)-2-[(R)-2-(3'-Chloro-biphenyl-4-yl)-1-(1-methyl-1H-tetrazol-5-ylcarbamoyl)-ethylamino]-propionic acid | 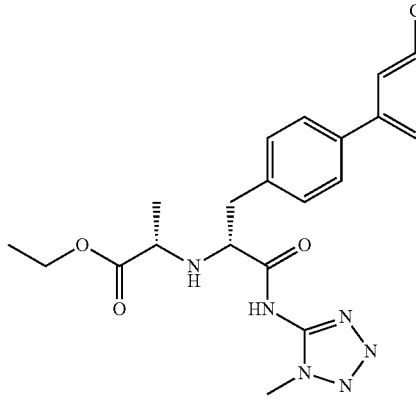<br>(S)-2-[(R)-2-(3'-Chloro-biphenyl-4-yl)-1-(1-methyl-1H-tetrazol-5-ylcarbamoyl)-ethylamino]-propionic acid ethyl ester | 2M NaOH aq, EtOH, RT | 1.43 min. (A) | 429 |
| Example 3-12 | 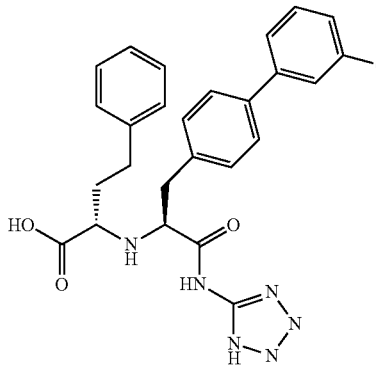<br>(S)-2-[(S)-2-(3'-Chloro-biphenyl-4-yl)-1-(1H-tetrazol-5-ylcarbamoyl)-ethylamino]-4-phenyl-butyric acid | 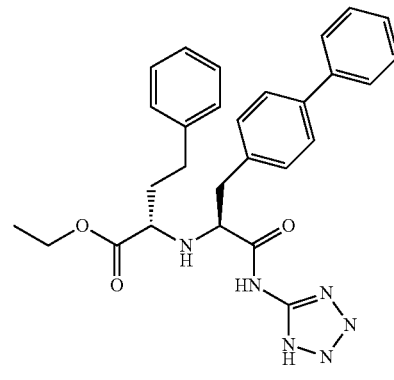<br>(S)-2-[(S)-2-(3'-Chloro-biphenyl-4-yl)-1-(1H-tetrazol-5-ylcarbamoyl)-ethylamino]-4-phenyl-butyric acid ethyl ester | 2M NaOH aq, EtOH, RT | 0.82 min. (B) | 505 |

-continued

| Example # | Product | Starting Material | Hydrolysis Condition | HPLC-RT (condition) | MS (M+1) |
|---|---|---|---|---|---|
| Example 3-13 | 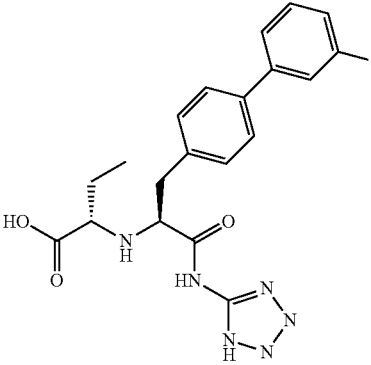<br>(S)-2-[(S)-2-(3'-Chloro-biphenyl-4-yl)-1-(1H-tetrazol-5-ylcarbamoyl)-ethylamino]-butyric acid | 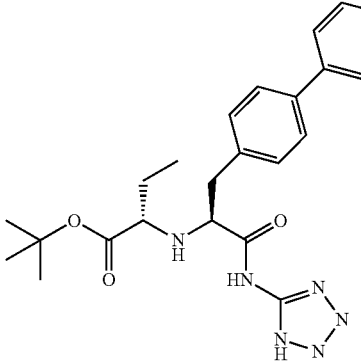<br>(S)-2-[(S)-2-(3'-Chloro-biphenyl-4-yl)-1-(1H-tetrazol-5-ylcarbamoyl)-ethylamino]-butyric acid tert-butyl ester | TFA, DCM, RT | 0.42 min. (C) | 429 |
| Example 3-14 | 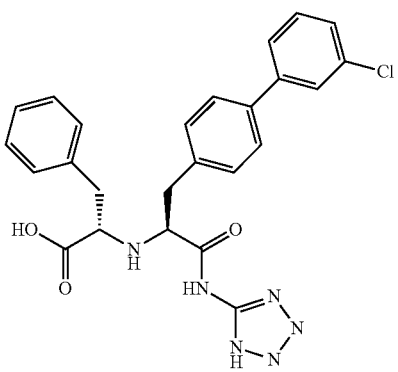<br>(S)-2-[(S)-2-(3'-Chloro-biphenyl-4-yl)-1-(1H-tetrazol-5-ylcarbamoyl)-ethylamino]-3-phenyl-propionic acid | 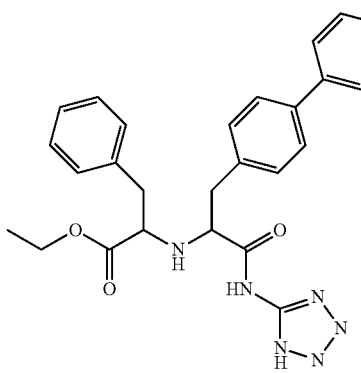<br>2-[2-(3'-Chloro-biphenyl-4-yl)-1-(1H-tetrazol-5-ylcarbamoyl)-ethylamino]-3-phenyl-propionic acid ethyl ester | 2M NaOH aq, EtOH, RT | 1.25 min. (A) | 491 |

| Example # | Product | Starting Material | Hydrolysis Condition | HPLC-RT (condition) | MS (M+1) |
|---|---|---|---|---|---|
| Example 3-15 | 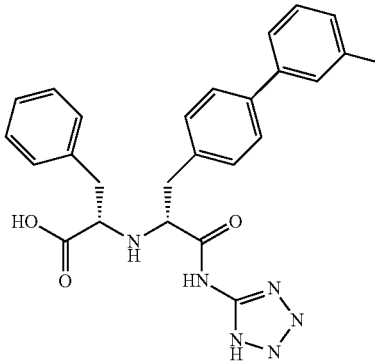<br>(S)-2-[(R)-2-(3'-Chloro-biphenyl-4-yl)-1-(1H-tetrazol-5-ylcarbamoyl)-ethylamino]-3-phenyl-propionic acid | 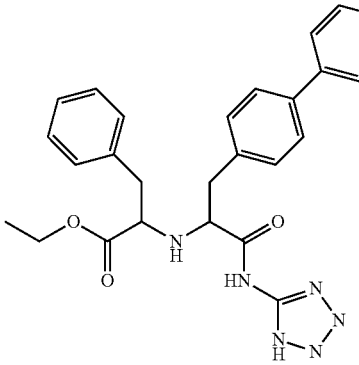<br>2-[2-(3'-Chloro-biphenyl-4-yl)-1-(1H-tetrazol-5-ylcarbamoyl)-ethylamino]-3-phenyl-propionic acid ethyl ester | 2M NaOH aq, EtOH, RT | 1.28 min. (A) | 491 |
| Example 3-16 | 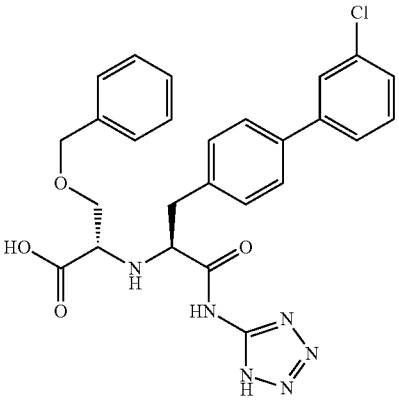<br>(S)-3-benzyloxy-2-[(S)-2-(3'-chloro-biphenyl-4-yl)-1-(1H-tetrazol-5-ylcarbamoyl)-ethylamino]-propionic acid | 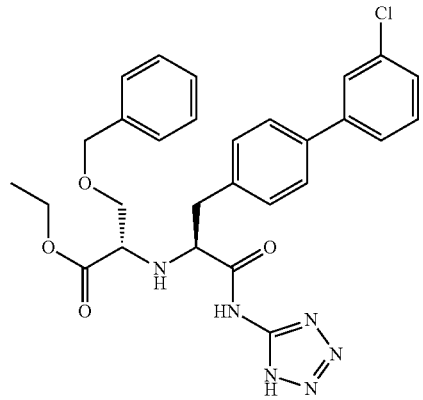<br>(S)-3-benzyloxy-2-[(S)-2-(3'-chloro-biphenyl-4-yl)-1-(1H-tetrazol-5-ylcarbamoyl)-ethylamino]-propionic acid ethyl ester | 2M NaOH aq, EtOH, RT | 1.35 min. (A) | 521 |

| Example # | Product | Starting Material | Hydrolysis Condition | HPLC-RT (condition) | MS (M+1) |
|---|---|---|---|---|---|
| Example 3-17 | 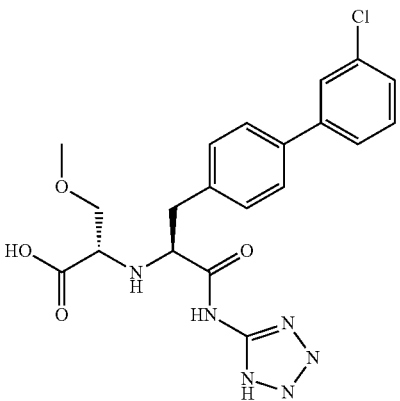<br>(S)-2-[(S)-2-(3'-chloro-biphenyl-4-yl)-1-(1H-tetrazol-5-ylcarbamoyl)-ethylamino]-3-methoxy-propionic acid | 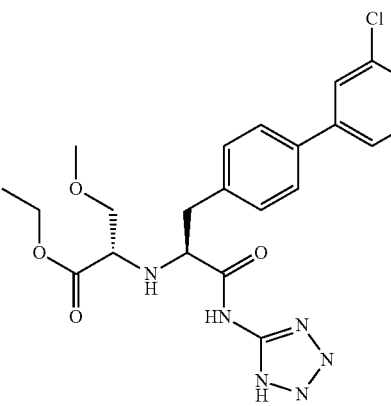<br>(S)-2-[(S)-2-(3'-chloro-biphenyl-4-yl)-1-(1H-tetrazol-5-ylcarbamoyl)-ethylamino]-3-methoxy-propionic acid ethyl ester | 2M NaOH aq, EtOH, RT | 0.93 min. (A) | 445 |
| Example 3-18 | 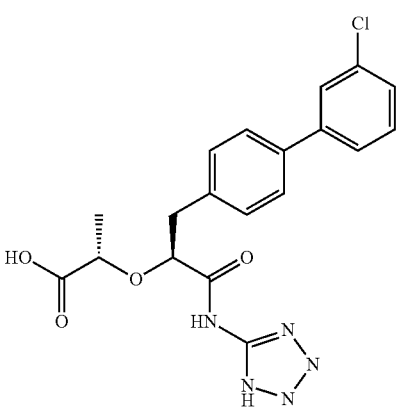<br>(S)-2-[(S)-2-(3'-chloro-biphenyl-4-yl)-1-(1H-tetrazol-5-ylcarbamoyl)-ethoxy]-propionic acid | 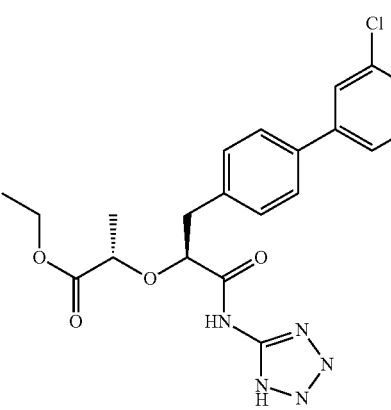<br>(S)-2-[(S)-2-(3'-chloro-biphenyl-4-yl)-1-(1H-tetrazol-5-ylcarbamoyl)-ethoxy]-propionic acid ethyl ester | 2M NaOH aq, MeOH, RT | 1.09 min (A) | 416 |

Example 3-3

$^1$H NMR (400 MHz, DMSO-d6+TFA-d) δ 1.48 (d, 3H, J=7.1 Hz), 3.27 (dd, 1H, J=8.8, 13.1 Hz), 3.47 (dd, 1H, J=6.1, 13.4 Hz), 4.03 (dd, 1H, J=7.1, 14.1 Hz), 4.47 (dd, 1H, J=7.3, 7.3 Hz), 7.37-7.42 (m, 5H), 7.47 (dd, 1H, J=2.8, 8.6 Hz), 7.58 (d, 1H, J=8.6 Hz), 14.89 (bs, 1H).

Example 3-4

$^1$H NMR (400 MHz, DMSO-d6) δ 1.37 (d, 3H, J=6.8 Hz), 3.20 (d, 2H, J=6.3 Hz), 3.73-3.87 (bs, 1H), 4.25-4.38 (bs, 1H), 7.33-7.38 (m, 1H), 7.36 (d, 2H, J=8.1 Hz), 7.45 (dd, 2H, J=7.4, 7.4 Hz), 7.60-7.66 (m, 4H).

Example 3-5

$^1$H NMR (400 MHz, DMSO-d6) δ 1.35-1.43 (m, 3H), 3.20 (bs, 2H), 3.71 (s, 3H), 3.75-4.00 (m, 1H), 4.36 (bs, 1H), 7.05-7.20 (m, 3H), 7.31 (d, 2H, J=8.3 Hz), 7.45 (d, 2H, J=8.3 Hz).

Example 3-6

$^1$H NMR (400 MHz, DMSO-d6+TFA-d) δ 1.48 (d, 3H, J=7.3 Hz), 3.22 (dd, 1H, J=7.6, 13.6 Hz), 3.32 (dd, 1H, J=6.6, 13.9 Hz), 3.96 (dd, 1H, J=7.3, 14.4 Hz), 4.50 (dd, 1H, J=7.3, 7.3 Hz), 6.97 (s, 1H), 7.33-7.38 (m, 3H), 7.45 (t, 2H, J=7.8 Hz), 7.61-7.67 (m, 4H).

Example 3-7

¹H NMR (400 MHz, DMSO-d6) δ 1.37 (bd, 3H, J=4.8 Hz), 3.09-3.26 (m, 2H), 3.67-3.90 (m, 1H), 4.10-4.37 (m, 1H), 5.83 (s, 1H), 7.34 (d, 2H, J=8.1 Hz), 7.40-7.45 (m, 1H), 7.48 (dd, 1H, J=7.8, 7.8 Hz), 7.61-7.66 (m, 1H), 7.66-7.73 (m, 3H).

Example 3-8

¹H NMR (400 MHz, DMSO-d6) δ 1.19-1.39 (m, 3H), 3.05-3.218 (m, 2H), 3.30-4.25 (m, 2H), 5.83 (s, 1H), 7.33 (d, 2H, J=8.3 Hz), 7.40-7.44 (m, 1H), 7.48 (dd, 1H, J=7.8, 7.8 Hz), 7.61-7.73 (m, 4H).

Example 3-9

¹H NMR (400 MHz, DMSO-d6) δ 1.48-1.57 (m, 3H), 3.05-3.47 (m, 2H), 3.728/3.31 (s×2, total 3H), 4.02-4.21 (m, 1H), 5.61-5.82 (m, 1H), 7.06-7.27 (m, 1H), 7.34-7.76 (m, 7H).

Example 3-10

¹H NMR (400 MHz, DMSO-d6) δ 1.35-1.43 (m, 3H), 3.13-3.34 (m, 2H), 3.35-3.95 (m, 1H), 3.73 (s, 3H), 4.08-4.45 (m, 1H), 7.39-7.45 (m, 3H), 7.49 (dd, 1H, J=7.8, 7.8 Hz), 7.62-7.75 (m, 4H).

Example 3-11

¹H NMR (400 MHz, DMSO-d6) δ 1.32-1.42 (m, 3H), 3.13-3.34 (m, 2H), 3.35-3.95 (m, 1H), 3.73 (s, 3H), 4.02-4.36 (m, 1H), 7.37-7.45 (m, 3H), 7.49 (dd, 1H, J=7.8, 7.8 Hz), 7.61-7.74 (m, 4H).

Example 3-12

¹H NMR (400 MHz, DMSO-$d_6$) δ ppm 1.67-1.90 (m, 2H), 2.59 (t, J=7.7 Hz, 2H), 2.96 (dd, J=13.6, 7.3 Hz, 1H), 3.07 (dd, J=13.6, 7.1 Hz, 1H), 3.11-3.17 (m, 1H), 3.78 (t, J=7.1 Hz, 1H), 7.07-7.18 (m, 5H), 7.33 (d, J=8.3 Hz, 2H), 7.37-7.42 (m, 1H), 7.46 (t, J=8.0 Hz, 1H), 7.61 (d, J=8.3 Hz, 3H), 7.68 (t, J=1.8 Hz, 1H), 12.02 (br. s., 1H), 15.89 (br. s., 1H).

Example 3-13

¹H NMR (400 MHz, DMSO-$d_6$) δ ppm 0.91 (t, J=7.5 Hz, 3H), 1.67-1.80 (m, 2H), 3.08-3.27 (m, 2H), 3.56 (br. s., 3H), 4.16 (br. s., 1H), 7.34 (d, J=8.3 Hz, 2H), 7.41 (ddd, J=7.8, 2.0, 1.0 Hz, 1H), 7.47 (t, J=7.8 Hz, 1H), 7.61 (dt, J=8.0, 1.5, 1.1 Hz, 1H), 7.64 (d, J=8.3 Hz, 2H), 7.68 (t, J=1.8 Hz, 1H), 12.27 (br. s., 1H), 16.09 (br. s., 1H).

Example 3-14

¹H NMR (400 MHz, DMSO-$d_6$) δ ppm 2.83-2.91 (m, 2H), 2.91-3.11 (m, 2H), 3.56 (br. s., 2H), 3.88 (br. s., 1H), 7.14-7.20 (m, 3H), 7.20-7.26 (m, 2H), 7.29 (d, J=8.3 Hz, 2H), 7.38-7.42 (m, 1H), 7.47 (t, J=7.8 Hz, 1H), 7.56-7.63 (m, 3H), 7.68 (t, J=1.9 Hz, 1H), 11.92 (br. s., 1H), 15.91 (br. s., 1H).

Example 3-15

¹H NMR (400 MHz, DMSO-$d_6$) δ ppm 2.81-3.03 (m, 4H), 3.51 (t, J=6.4 Hz, 1H), 3.79 (t, J=6.2 Hz, 1H), 7.14-7.29 (m, 7H), 7.38-7.42 (m, 1H), 7.47 (t, J=7.8 Hz, 1H), 7.55 (d, J=8.1 Hz, 2H), 7.59 (dt, J=7.6, 1.4 Hz, 1H), 7.66 (t, J=1.9 Hz, 1H), 11.78 (br. s., 1H), 15.86 (br. s., 1H).

Example 3-16

¹H NMR (400 MHz, DMSO-$d_6$) δ ppm 2.97 (dd, 1H, J=7.1, 13.6 Hz), 3.07 (dd, 1H, J=6.3, 13.6 Hz), 3.47 (dd, 1H, J=5.1, 5.1 Hz), 3.58 (d, 2H, J=5.1 Hz), 3.87 (dd, 1H, J=6.6 Hz), 4.41 (d, 1H, J=12.4 Hz), 4.46 (d, 1H, J=12.1 Hz), 7.22-7.36 (m, 7H), 7.38-7.42 (m, 1H), 7.47 (t, 1H, j=7.8 Hz), 7.58-7.64 (m, 3H), 7.68 (t, 1H, J=1.8 Hz).

Example 3-17

¹H NMR (400 MHz, DMSO-$d_6$) δ ppm 2.97-3.13 (m, 2H), 3.21 (s, 3H), 3.40-3.61 (m, 3H), 3.76-4.01 (m, 1H), 7.34 (d, J=8.34 Hz, 2H), 7.38-7.43 (m, 1H), 7.47 (t, J=8.08 Hz, 1H), 7.59-7.65 (m, 3H), 7.69 (bt, J=1.77 Hz, 1H).

Example 3-18

1H NMR (400 MHz, DMSO-$d_6$) d ppm 1.31 (d, J=6.6 Hz, 3H), 3.05-3.18 (m, 2H), 4.03 (q, J=6.8 Hz, 1H), 4.58 (t, J=6.3 Hz, 1H), 7.35 (d, J=8.1 Hz, 2H), 7.37-7.42 (m, 1H), 7.47 (t, J=7.8 Hz, 1H), 7.55-7.65 (m, 3H), 7.66-7.72 (m, 1H), 12.13 (br. s., 1H), 12.69 (br. s., 1H), 15.96 (br. s., 1H)

Example 3-19

(S)-2-[(S)-2-(3'-chloro-biphenyl-4-yl)-1-(1H-tetrazol-5-ylcarbamoyl)-ethylamino]-3-hydroxy-propionic acid

Example 3-20

(S)-2-[(S)-2-biphenyl-4-yl-1-(1H-tetrazol-5-ylcarbamoyl)-ethylamino]-3-hydroxy-propionic acid

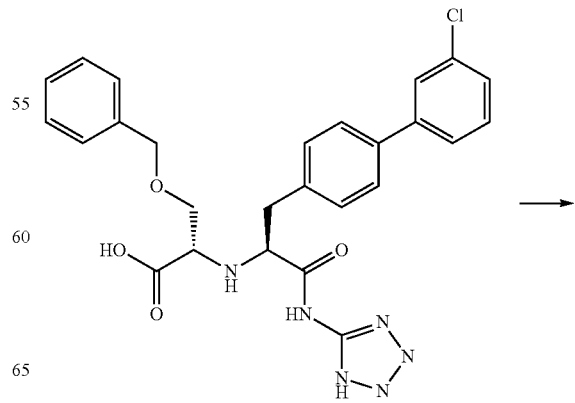

83
-continued

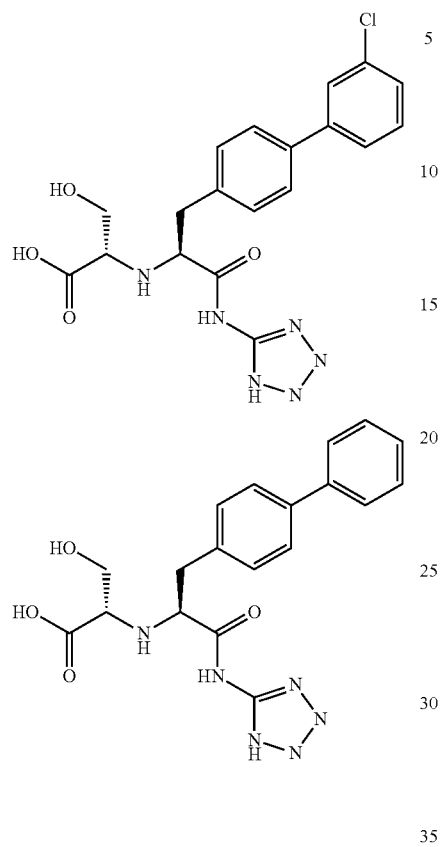

To a solution of (S)-3-benzyloxy-2-[(S)-2-(3'-chloro-biphenyl-4-yl)-1-(1H-tetrazol-5-ylcarbamoyl)-ethylamino]-propionic acid ethyl ester (47 mg, 0.090 mmol) in EtOAc (1 mL) and EtOH (1 mL) was added 5% Pd—C (9.6 mg, 0.0045 mmol). H₂ gas was loaded with a balloon and the reaction mixture was stirred at 50° C. for 6 hours. The reaction mixture was filtered through celite pad and the filtrate was concentrated. The residue was purified by reverse phase HPLC (Sunfire C-18 column, eluent: 0.1% TFA in H₂O/CH3CN) to give (S)-2-[(S)-2-(3'-chloro-biphenyl-4-yl)-1-(1H-tetrazol-5-ylcarbamoyl)-ethylamino]-3-hydroxy-propionic acid and (S)-2-[(S)-2-biphenyl-4-yl-1-(1H-tetrazol-5-ylcarbamoyl)-ethylamino]-3-hydroxy-propionic acid.

(S)-2-[(S)-2-(3'-chloro-biphenyl-4-yl)-1-(1H-tetrazol-5-ylcarbamoyl)-ethylamino]-3-hydroxy-propionic acid; NMR (400 MHz, DMSO-d6) δ ppm 2.99-3.14 (m, 2H), 3.50-3.67 (m, 3H), 3.86-3.98 (m, 1H), 7.34 (d, 2H, J=8.3 Hz), 7.38-7.42 (m, 1H), 7.47 (t, 2H, J=7.8 Hz), 7.58-7.70 (m, 4H)); HPLC Retention time 1.17 minutes (condition A); MS: m/z (MH+) 431.

(S)-2-[(S)-2-biphenyl-4-yl-1-(1H-tetrazol-5-ylcarbamoyl)-ethylamino]-3-hydroxy-propionic acid; NMR (400 MHz, DMSO-d6) δ ppm 3.18 (dd, 1H, J=7.6, 13.4 Hz), 3.24-3.36 (m, 1H), 3.66-3.87 (m, 3H), 4.17-4.37 (m, 1H), 7.32 (d, 2H, J=8.1 Hz), 7.32-7.38 (m, 1H), 7.44 (t, 2H, J=7.8 Hz), 7.56-7.67 (m, 4H)); HPLC Retention time 1.00 minutes (condition A); MS: m/z (MH+) 397.

84
Example 4-1

(S)-3-(3'-chloro-biphenyl-4-yl)-2-((S)-2-methane-sulfonylamino-1-methyl-2-oxo-ethylamino)-N-(1H-tetrazol-5-yl)-propionamide

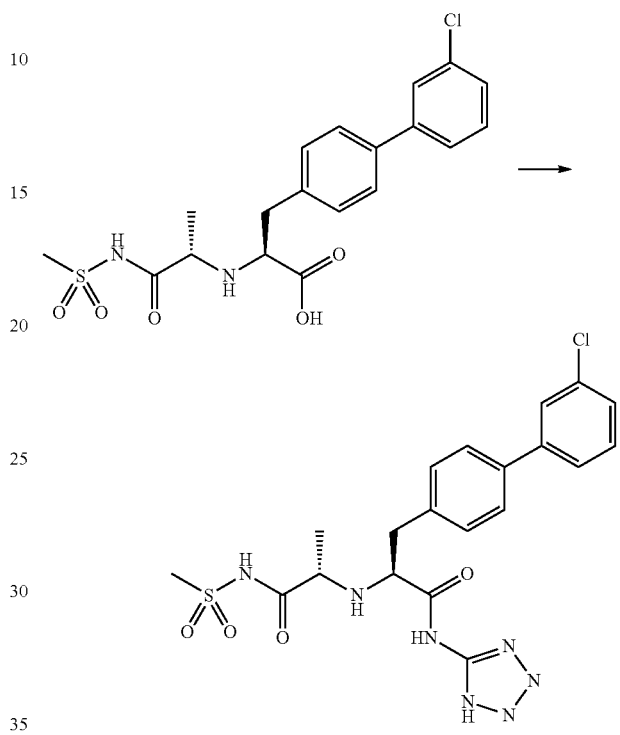

Example 4-1 was prepared using similar procedure as example 1-1. NMR (400 MHz, DMSO-d6+TFA-d) δ 1.21 (d, J=6.32 Hz, 3H), 2.92-3.05 (m, 1H), 3.05-3.14 (m, 1H), 3.17 (s, 3H), 3.34-3.46 (m, 1H), 3.82-3.95 (m, 1H), 7.35 (d, J=8.08 Hz, 2H), 7.39-7.43 (m, 1H), 7.47 (t, J=7.83 Hz), 7.60-7.66 (m, 3H), 7.68-7.22 (m, 1H)); HPLC Retention time 1.21 minutes (condition A); MS: m/z (MH+) 492.

Starting materials or intermediates were prepared in following manner:

Intermediate 1

(S)-3-(3'-Chloro-biphenyl-4-yl)-2-((S)-1-ethoxycarbonyl-ethylamino)-propionic acid

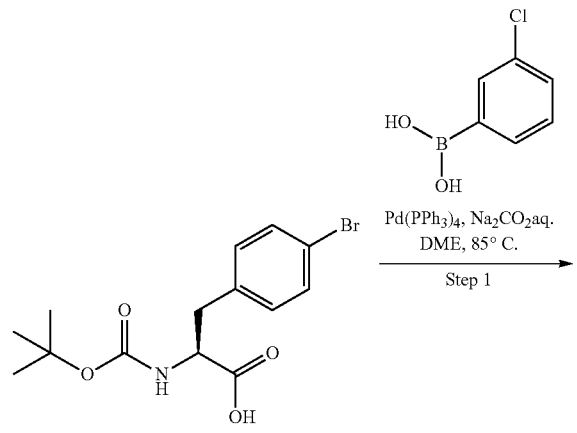

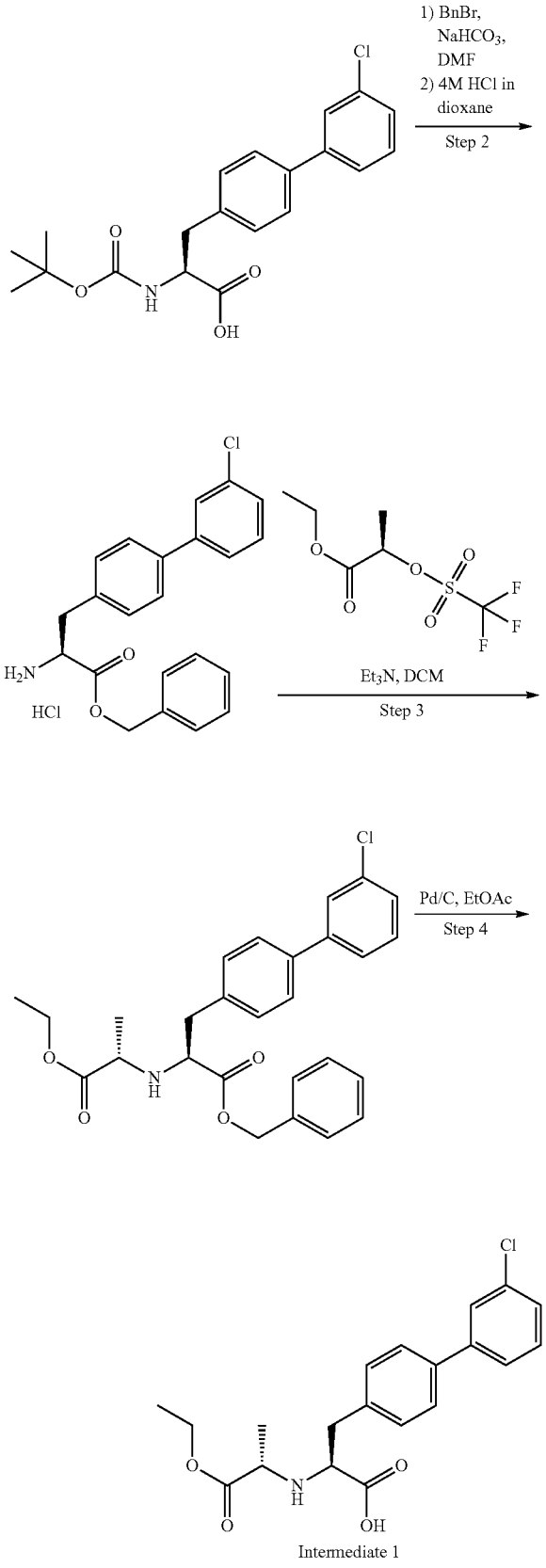

Intermediate 1

Step 1: To a solution of Boc-L-4-bromophenylalanine (15.0 g, 43.6 mmol), 3-chlorophenylboronic acid (8.52 g, 54.5 mmol), and tetrakis(triphenylphosphine)palladium(0) (1.51 g, 1.31 mmol) in 1,2-dimethoxyethane (180 mL) was added 2M solution of aqueous $NaCO_3$ (33 mL). The reaction mixture was heated to 85° C. After stirred for 2 hours, the reaction mixture was cooled to room temperature and diluted with EtOAc. The mixture was washed with 1M HCl and brine. The organic layer was dried over $Na_2SO_4$, concentrated under reduced pressure, and purified by silica gel column chromatography (eluent: 10% MeOH in dichloromethane) to give (S)-2-tert-butoxycarbonylamino-3-(3'-chloro-biphenyl-4-yl)-propionic acid (13.6 g). $^1$H NMR (400 MHz, $CDCl_3$) δ 1.43 (s, 9H), 3.08-3.17 (m, 1H), 3.21-3.31 (m, 1H), 4.65 (bs, 1H), 5.01 (bs, 1H), 7.23-7.32 (m, 3H), 7.45-7.50 (m, 2H), 7.52-7.60 (m, 1H), 7.63-7.70 (m, 2H); MS: m/z ($MH^+$) 376.

Step 2: To a solution of (S)-2-tert-butoxycarbonylamino-3-(3'-chloro-biphenyl-4-yl)-propionic acid (12.9 g, 34.3 mmol) in DMF (130 mL) were added benzyl bromide (8.16 mL, 68.6 mmol) and $NaHCO_3$ (5.77 g, 68.6 mmol). After stirred at room temperature overnight, the reaction mixture was diluted with EtOAc. The mixture was washed with $H_2O$ and brine, dried over $Na_2SO_4$, and concentrated under reduced pressure. The obtained residue was treated with 4M HCl in dioxane (30 mL) and stirred for 2 hours. The reaction mixture was concentrated and the resulted residue was rinsed with $iPr_2O$ to give (S)-2-amino-3-(3'-chloro-biphenyl-4-yl)-propionic acid benzyl ester (11.2 g). $^1$H NMR (400 MHz, DMSO-d6) δ 3.14 (dd, 1H, J=7.7, 12.0 Hz), 3.27 (dd, 1H, J=5.9, 12.0 Hz), 4.38 (dd, 1H, J=5.9, 7.7 Hz), 5.15 (s, 2H), 7.23-7.27 (m, 2H), 7.30-7.34 (m, 5H), 7.42-7.45 (m, 1H), 7.51 (dd, 1H, J=7.6, 7.6 Hz), 7.61-7.66 (m, 3H), 7.69 (dd, 1H, J=1.8, 1.8 Hz), 8.64 (bs, 2H); MS: m/z ($MH^+$) 366.

Step 3: To a solution of (S)-2-amino-3-(3'-chloro-biphenyl-4-yl)-propionic acid benzyl ester (10.0 g, 24.9 mmol) in dichloromethane (100 mL) was added triethylamine (10.4 mL, 74.6 mmol) at 0° C. After stirred for 10 min, ethyl (R)-2-(trifluoromethylsulfonyloxy)propionate (9.3 mL, 49.5 mmol) was added at room temperature and stirred for 1 hour. Additional triethylamine (10.4 mL, 74.6 mmol) and ethyl (R)-2-(trifluoromethylsulfonyloxy)propionate (9.3 mL, 49.5 mmol) were added at room temperature and stirred for additional 2 hours. The reaction mixture was washed with $H_2O$ and the organic layer was concentrated under reduced pressure. The obtained residue was purified by silica gel column chromatography (EtOAc/heptane) to give (S)-3-(3'-chloro-biphenyl-4-yl)-2-((S)-1-ethoxycarbonyl-ethylamino)-propionic acid benzyl ester (10.6 g). $^1$H NMR (400 MHz, $CDCl_3$) δ 1.21 (t, 3H, J=7.3 Hz), 1.27 (d, 3H, J=6.8 Hz), 1.89 (bs, 1H), 2.95-3.07 (m, 2H), 3.38 (dd, 1H, J=6.8, 14.8 Hz), 3.69 (dd, 1H, J=7.1, 7.1 Hz), 4.06-4.17 (m, 2H), 5.06 (d, 1H, J=12.1 Hz), 5.12 (d, 1H, J=12.1 Hz), 7.20-7.25 (m, 4H), 7.28-7.34 (m, 4H), 7.35 (dd, 1H, J=7.6, 7.6 Hz), 7.41-7.46 (m, 3H), 7.53 (dd, 1H, J=1.5, 1.5 Hz); MS: m/z ($MH^+$) 466.

Step 4: A suspension of (S)-3-(3'-chloro-biphenyl-4-yl)-2-((S)-1-ethoxycarbonyl-ethylamino)-propionic acid benzyl ester (10.0 g, 21.5 mmol) and 5% Pd on carbon (0.914 g) in EtOAc (200 mL) was treated with $H_2$ (balloon) and stirred at 10-15° C. for 1.5 hour and at room temperature for 0.5 hour.

The resulted precipitate was dissolved in methanol and filtered through celite pad. The filtrate was concentrated under reduced pressure and the obtained residue was re-crystallized from EtOAc to give (S)-3-(3'-chloro-biphenyl-4-yl)-2-((S)-1-ethoxycarbonyl-ethylamino)-propionic acid (5.6 g). The mother liquor was concentrated under reduced pressure and purified by silica gel column chromatography to give additional amount of (S)-3-(3'-chloro-biphenyl-4-yl)-2-((S)-1-ethoxycarbonyl-ethylamino)-propionic acid (1.4 g). $^1$H NMR (400 MHz, DMSO-d6) δ 1.13 (t, 3H, J=7.1 Hz), 1.15 (d, 3H, J=6.8 Hz), 2.85 (dd, 1H, J=7.1, 14.1 Hz), 2.93 (dd, 1H, J=6.3, 13.6 Hz), 3.30-3.37 (m, 1H), 3.48 (dd, 1H, J=6.5, 6.5 Hz), 4.03 (q, 2H, J=7.1 Hz), 7.32 (d, 2H, J=8.3 Hz), 7.38-7.43 (m, 1H), 7.48 (dd, 1H, J=7.8, 7.8 Hz), 7.59-7.65 (m, 3H), 7.70 (dd, 1H, J=2.0, 2.0 Hz); MS: m/z (MH$^+$) 376.

Intermediate 2

(S)-2-((S)-1-tert-Butoxycarbonyl-ethylamino)-3-(2',5'-dichloro-biphenyl-4-yl)-propionic acid

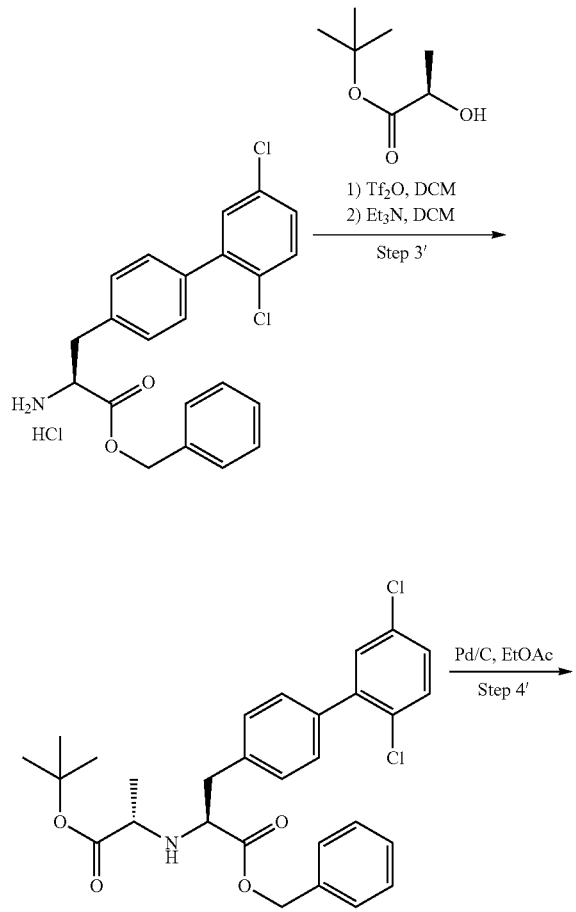

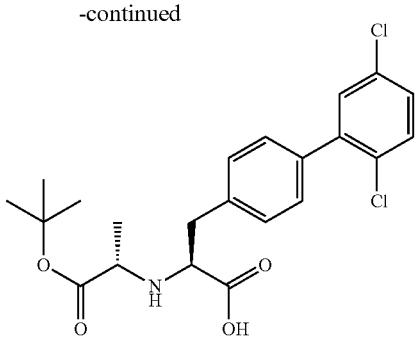

Same procedures described in step 1 (2,5-dichlorophenylboronic acid was used instead of 3-chlorophenylboronic acid) and step 2 for the preparation of intermediate 1 were used to prepare ((S)-2-amino-3-(2',5'-dichloro-biphenyl-4-yl)-propionic acid benzyl ester hydrochloride.

Step 3': t-Butyl (R)-2-(trifluoromethylsulfonyloxy)propionate was prepared from (R)-2-hydroxy-propionic acid tert-butyl ester (602 mg, 4.12 mmol), triflic anhydride (0.696 mL, 4.12 mmol) and 2,6-lutidine (0.480 mL, 4.12 mmol) in DCM (5 mL). To a suspension of ((S)-2-amino-3-(2',5'-dichloro-biphenyl-4-yl)-propionic acid benzyl ester hydrochloride (600 mg, 1.38 mmol) in dichloromethane (10 mL) was added triethylamine (0.574 mL, 4.12 mmol) at 0° C. After stirred for 10 min, a half amount of the freshly prepared t-butyl (R)-2-(trifluoromethylsulfonyloxy)propionate was added at room temperature and stirred for 1 hour. Additional triethylamine (0.574 mL, 4.12 mmol) and the rest of t-butyl (R)-2-(trifluoromethylsulfonyloxy)propionate were added at room temperature and stirred for additional 2 hours. The reaction mixture was washed with H$_2$O and the organic layer was concentrated under reduced pressure. The obtained residue was purified by silica gel column chromatography (EtOAc/heptane) to give (S)-2-((S)-1-tert-butoxycarbonyl-ethylamino)-3-(2',5'-dichloro-biphenyl-4-yl)-propionic acid benzyl ester (580 mg). $^1$H NMR (400 MHz, CDCl$_3$) δ 1.24 (t, 3H, J=6.8 Hz), 1.41 (s, 9H), 3.00-3.07 (m, 2H), 3.26 (dd, 1H, J=7.1, 13.9 Hz), 3.70 (dd, 1H, J=7.1, 7.1 Hz), 5.09 (s, 2H), 7.20-7.42 (m, 12H); MS: m/z (MH$^+$) 528.

Step 4': A suspension of (S)-2-((S)-1-tert-Butoxycarbonyl-ethylamino)-3-(2',5'-dichloro-biphenyl-4-yl)-propionic acid benzyl ester (580 mg, 1.10 mmol) and 5% Pd on carbon (0.146 g) in EtOAc (10 mL) was treated with H$_2$ (balloon) and stirred at rt for 1.5 hour. The resulted precipitate was dissolved in methanol and filtered through celite pad. The filtrate was concentrated under reduced pressure and the obtained residue was re-crystallized from EtOAc to give (S)-2-((S)-1-tert-butoxycarbonyl-ethylamino)-3-(2',5'-dichloro-biphenyl-4-yl)-propionic acid (438 mg). $^1$H NMR (400 MHz, DMSO-d6) δ 1.12 (d, 3H, J=7.1 Hz), 1.35 (s, 9H), 2.84 (dd, 2H, J=7.3, 13.6 Hz), 2.95 (dd, 2H, J=6.1, 13.6 Hz), 3.20 (dd, 1H, J=6.8, 13.6 Hz), 3.48 (dd, 1H, J=6.1, 7.3 Hz), 7.33 (d, 2H, J=8.6 Hz), 7.37 (d, 2H, J=8.3 Hz), 7.42-7.49 (m, 2H), 7.60 (d, 2H, J=8.6 Hz); MS: m/z (MH$^+$) 438.

Following intermediates were prepared using similar procedure as intermediate 1 or intermediate 2 with appropriate reagent:

| Intermediate # | Intermediate | Reagent | HPLC-RT (condition) | MS (M + 1) |
|---|---|---|---|---|
| Intermediate 3 | 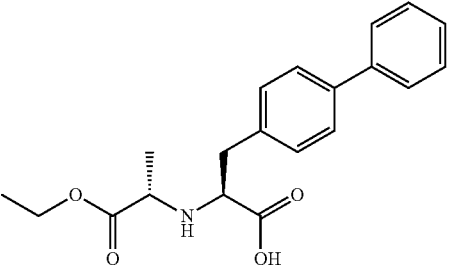<br>(S)-3-Biphenyl-4-yl-2-((S)-1-ethoxy-carbonyl-ethylamino)-propionic acid | phenylboronic acid was used instead of 3-chlorophenylboronic acid in step 1 | 0.71 min (C) | 342 |
| Intermediate 4 | 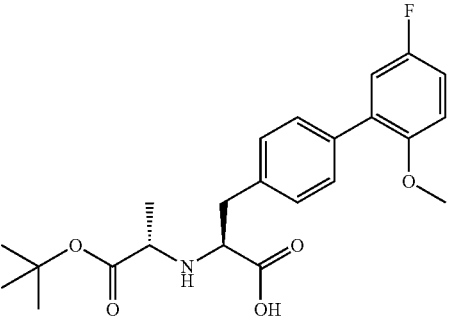<br>(S)-2-((S)-1-tert-Butoxycarbonyl-ethylamino)-3-(5'-fluoro-2'-methoxy-biphenyl-4-yl)-propionic acid | 2-methoxy-5-fluoro-phenylboronic acid was used instead of 3-chlorophenylboronic acid in step 1 | 1.07 min (C) | 418 |
| Intermediate 5 | 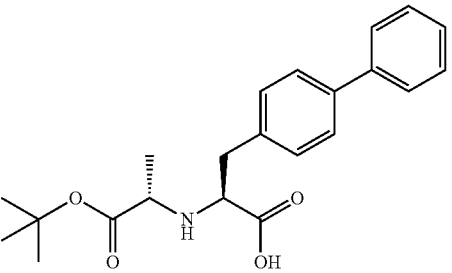<br>(S)-3-Biphenyl-4-yl-2-((S)-1-tert-butoxycarbonyl-ethylamino)-propionic acid | phenylboronic acid was used instead of 3-chlorophenylboronic acid in step 1 | 1.05 min (C) | 370 |

-continued

| Intermediate # | Intermediate | Reagent | HPLC-RT (condition) | MS (M + 1) |
|---|---|---|---|---|
| Intermediate 6 | 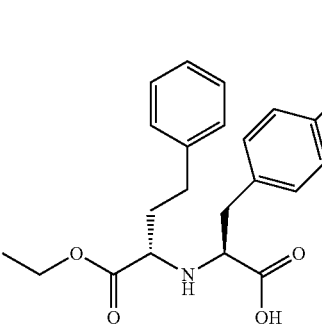<br>(S)-2-[(S)-1-carboxy-2-(3'-chloro-biphenyl-4-yl)-ethylamino]-4-phenyl-butyric acid ethyl ester | (R)-2-Hydroxy-4-phenyl-butyric acid ethyl ester was used instead of (R)-2-hydroxy-propionic acid tert-butyl ester in Step 3' | 1.39 min (C) | 466 |
| Intermediate 7 | 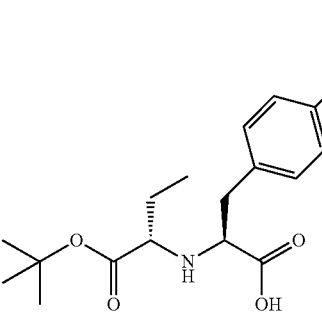<br>(S)-2-[(S)-1-Carboxy-2-(3'-chloro-biphenyl-4-yl)-ethylamino]-butyric acid tert-butyl ester | (R)-2-Hydroxy-butyric acid tert-butyl ester was used instead of (R)-2-hydroxy-propionic acid tert-butyl ester in Step 3' | 1.15 min (C) | 418 |
| Intermediate 8 | 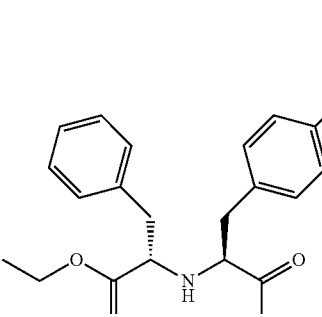<br>(S)-3-(3'-Chloro-biphenyl-4-yl)-2-((S)-1-ethoxycarbonyl-2-phenyl-ethyl-amino)-propionic acid | (R)-2-Hydroxy-3-phenyl-propionic acid ethyl ester was used instead of (R)-2-hydroxy-propionic acid tert-butyl ester in Step 3' | 1.27 min (C) | 452 |

Intermediate 9: [1-(4-Methoxy-benzyl)-1H-tetrazol-5-yl]-methyl-amine

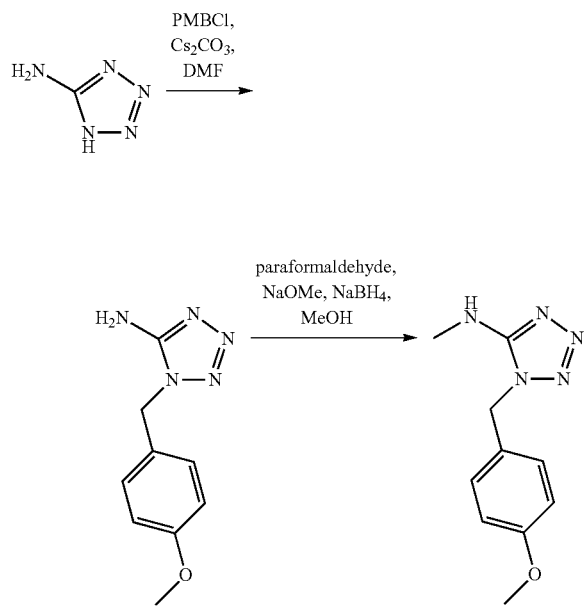

To a suspension of 5-amino-1H-tetrazole (1.50 g, 17.6 mmol) in DMF (30 mL) were added $Cs_2CO_3$ (8.62 g, 26.4 mmol) and PMBCl (2.90 g, 18.5 mmol). After stirred at 60° C. for 3 hours, the reaction mixture was cooled to room temperature and diluted with EtOAc. The mixture was washed with $H_2O$ and brine, dried over $Na_2SO_4$, and concentrated under reduced pressure. The residue was diluted with DCM and the resulted precipitate was collected by filtration to give 1-(4-methoxy-benzyl)-1H-tetrazol-5-ylamine (0.625 g). $^1$H NMR (400 MHz, DMSO-d6) δ 3.73 (s, 3H), 5.27 (s, 2H), 6.78 (s, 2H), 6.92 (d, 2H, J=8.8 Hz), 7.21 (d, 2H, J=8.8 Hz).

Next, to a suspension of 1-(4-methoxy-benzyl)-1H-tetrazol-5-ylamine (600 mg, 2.92 mmol) in MeOH (10 mL) were added paraformaldehyde (132 mg, 4.39 mmol) and sodium methoxide (632 mg, 25 wt % in MeOH). The mixture was refluxed for 30 min until the suspension turned into a clear solution. The mixture was cooled to room temperature and sodium borohydride (332 mg, 8.77 mmol) was added portionwise. The reaction mixture was refluxed again for 15 min. After cooled to room temperature, the reaction was quenched with $H_2O$. The mixture was diluted with EtOAc, partially concentrated, and washed with brine. The organic layer was dried over $Na_2SO_4$ and concentrated under reduced pressure. The residue was purified by silica gel column chromatography (eluent: 10% MeOH in DCM) to give [1-(4-methoxy-benzyl)-1H-tetrazol-5-yl]-methyl-amine (0.63 g). $^1$H NMR (400 MHz, $CDCl_3$) δ 3.00 (d, 3H, J=5.3 Hz), 3.61 (bs, 1H), 3.82 (s, 3H), 5.25 (s, 2H), 6.91 (d, 2H, J=8.8 Hz), 7.16 (d, 2H, J=8.8 Hz); MS: m/z (MH$^+$) 220.

Following intermediates were prepared using similar procedure as intermediate 1 or intermediate 2 with appropriate reagent:

| Intermediate # | Intermediate | Reagent | HPLC-RT (condition) | MS (M + 1) |
|---|---|---|---|---|
| Intermediate 9 | (S)-2-((S)-2-benzyloxy-1-ethoxycarbonyl-ethylamino)-3-(3'-chloro-biphenyl-4-yl)-propionic acid | (R)-3-Benzyloxy-2-hydroxy-propionic acid ethyl ester was used instead of (R)-2-hydroxy-propionic acid ethyl ester in Step 3 | 1.41 min (C) | 482 |

| Intermediate # | Intermediate | Reagent | HPLC-RT (condition) | MS (M + 1) |
|---|---|---|---|---|
| Intermediate 10 | 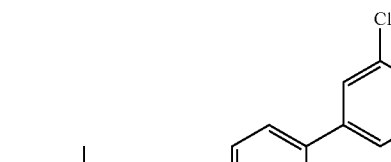<br>(S)-3-(3'-chloro-biphenyl-4-yl)-2-((S)-1-ethoxycarbonyl-2-methoxy-ethylamino)-propionic acid | (R)-2-Hydroxy-3-methoxy-propionic acid ethyl ester was used instead of (R)-2-hydroxy-propionic acid ethyl ester in Step 3 | 0.56 min (C) | 496 |

Intermediate 11: (S)-3-(3'-chloro-biphenyl-4-yl)-2-((S)-1-ethoxycarbonyl-ethoxy)-propionic acid

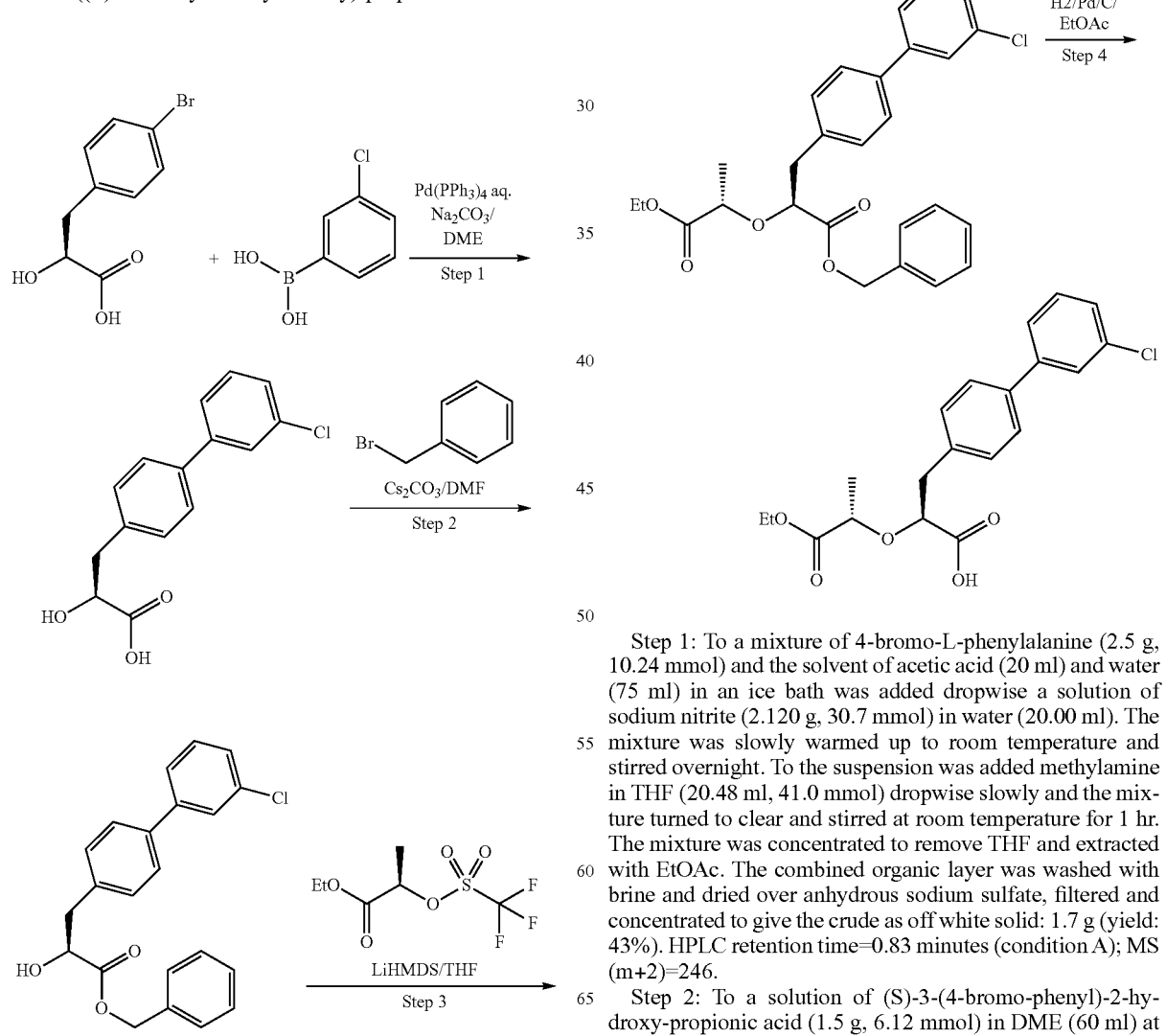

Step 1: To a mixture of 4-bromo-L-phenylalanine (2.5 g, 10.24 mmol) and the solvent of acetic acid (20 ml) and water (75 ml) in an ice bath was added dropwise a solution of sodium nitrite (2.120 g, 30.7 mmol) in water (20.00 ml). The mixture was slowly warmed up to room temperature and stirred overnight. To the suspension was added methylamine in THF (20.48 ml, 41.0 mmol) dropwise slowly and the mixture turned to clear and stirred at room temperature for 1 hr. The mixture was concentrated to remove THF and extracted with EtOAc. The combined organic layer was washed with brine and dried over anhydrous sodium sulfate, filtered and concentrated to give the crude as off white solid: 1.7 g (yield: 43%). HPLC retention time=0.83 minutes (condition A); MS (m+2)=246.

Step 2: To a solution of (S)-3-(4-bromo-phenyl)-2-hydroxy-propionic acid (1.5 g, 6.12 mmol) in DME (60 ml) at room temperature was added 3-chlorobenzeneboronic acid (1.436 g, 9.18 mmol) and followed by aq. Na$_2$CO$_3$ (6.12 ml, 12.24 mmol) and Pd(Ph$_3$P)$_4$ (0.212 g, 0.184 mmol). The mixture was stirred at 85° C. overnight. The reaction was added more EtOAc and acidified by 1N HCl to PH-5. The combined organic layer was washed with brine and dried over anhydrous sodium sulfate, filtered and concentrated. The residue was purified by HPLC (20 to 80% ACN—H$_2$O (0.1% TFA)) to give the white solid: 550 mg (yield: 32%). HPLC retention time=1.23 minutes (condition A); MS (m−1)=275.

Step 3: To a solution of (S)-3-(3'-chloro-biphenyl-4-yl)-2-hydroxy-propionic acid benzyl ester (282 mg, 0.769 mmol) in THF (6 ml) at −78° C. was added LiHMDS/THF (1.999 ml, 1.999 mmol) and the resulting yellow mixture was stirred at −78° C. for 25 mins then was added (R)-ethyl 2-(trifluoromethylsulfonyloxy)propanoate (0.860 ml, 4.61 mmol) at −20° C. 1 hr the reaction was almost complete. The reaction was quenched by sat. NH4Cl and was extracted with EtOAc. The combined organic layer was washed with brine, filtered and concentrated. The residue was purified by HPLC (75 to 100% ACN—H$_2$O (0.1% TFA)) to give the product: 140 mg (yield: 39%). HPLC retention time=1.57 minutes (condition C); MS (m+1)=467.

Step 4: A mixture of (S)-3-(3'-chloro-biphenyl-4-yl)-2-((S)-1-ethoxycarbonyl-ethoxy)-propionic acid benzyl ester and 10% Pd/C wet in EtOAc was hydrogenated under H$_2$ balloon for 30 mins. The reaction was filtered off the catalyst and concentrated. The residue was purified by HPLC (15 to 70% ACN—H$_2$O (0.1% TFA)) to give oil: 128 mg. HPLC retention time=1.07 minutes (condition C); MS (m−1)=375.

Intermediate 12

(S)-3-(3'-chloro-biphenyl-4-yl)-2-((S)-2-methane-sulfonylamino-1-methyl-2-oxo-ethylamino)-propionic acid

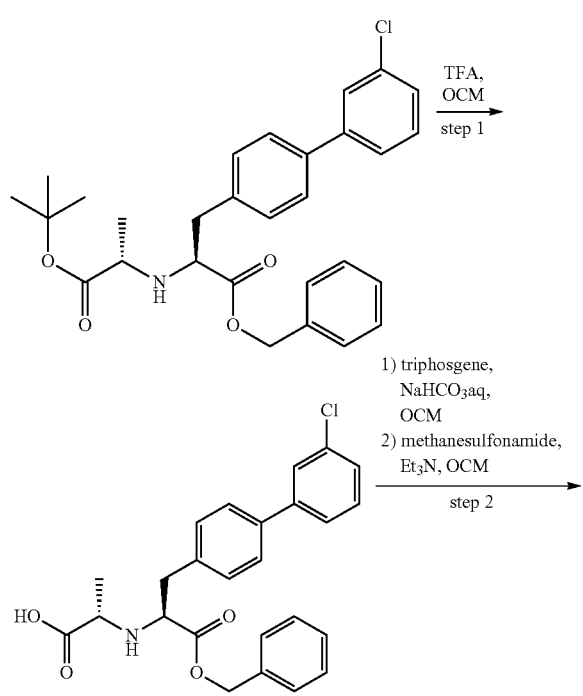

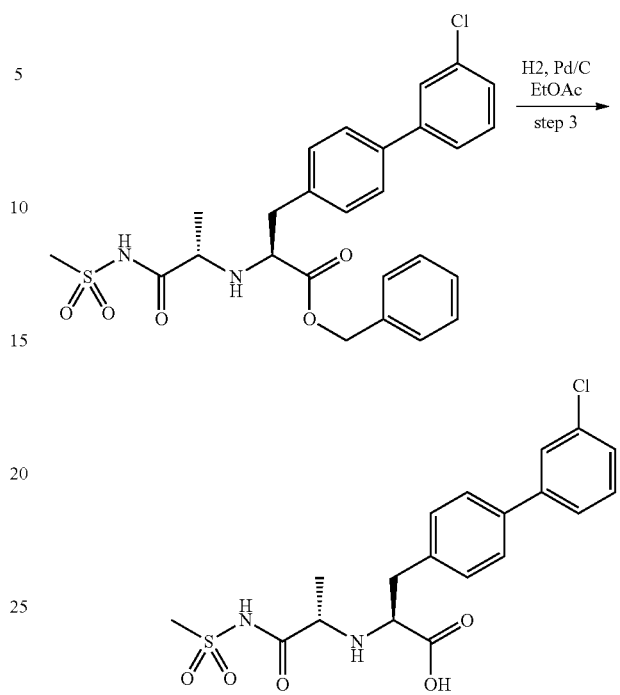

Step 1: To a solution of (S)-2-((S)-1-tert-butoxycarbonyl-ethylamino)-3-(3'-chloro-biphenyl-4-yl)-propionic acid benzyl ester (1.12 g, 2.27 mmol) in DCM (5 mL) was added TFA (5 mL). After being stirred for 3 hours, the reaction mixture was concentrated and purified by silica gel column chromatography (eluent: 10% MeOH in DCM) to give (S)-2-((S)-1-carboxy-ethylamino)-3-(3'-chloro-biphenyl-4-yl)-propionic acid benzyl ester. MS: m/z (MH$^+$) 438; HPLC retention time 0.73 min (HPLC condition C).

Step 2: To a solution of (S)-2-((S)-1-carboxy-ethylamino)-3-(3'-chloro-biphenyl-4-yl)-propionic acid benzyl ester (600 mg, 1.37 mmol) in DCM (7 mL) and saturated aqueous NaHCO$_3$ solution (2mL) was added triphosgene (407 mg, 1.37 mmol). After being stirred for 0.5 hours, the reaction mixture was diluted with EtOAc and stirred for additional 0.5 hours until generation of gas was completed. The organic layer was separated, washed with brine and concentrated. This was dissolved in DCM (7 mL) and methanesulfonamide (195 mg, 2.06 mmol) was added. After being stirred at rt for 1 hour, the reaction mixture was diluted with EtOAc and washed with brine. The organic layer was dried over Na$_2$SO$_4$, concentrated and purified by silica gel column chromatography (eluent: 10% MeOH in DCM) to give (S)-3-(3'-chloro-biphenyl-4-yl)-2-((S)-2-methanesulfonylamino-1-methyl-2-oxo-ethylamino)-propionic acid benzyl ester. MS: m/z (MH$^+$) 515; HPLC retention time 1.58 min (HPLC condition A).

Step 3: This was dissolved in EtOAc. 5% Pd—C (146 mg) was added and hydrogenated with H$_2$ balloon at rt for 1 hour. The reaction mixture was filtered through celite pad and the filtrate was concentrated. The resultant solid was re-crystallized from MeOH to give (S)-3-(3'-chloro-biphenyl-4-yl)-2-((S)-2-methanesulfonylamino-1-methyl-2-oxo-ethylamino)-propionic acid. MS: m/z (MH$^+$) 425; HPLC retention time 1.14 min (HPLC condition A).

Intermediate 12-2

(S)-2-((S)-1-tert-butoxycarbonyl-ethylamino)-3-(3'-chloro-biphenyl-4-yl)-propionic acid benzyl ester

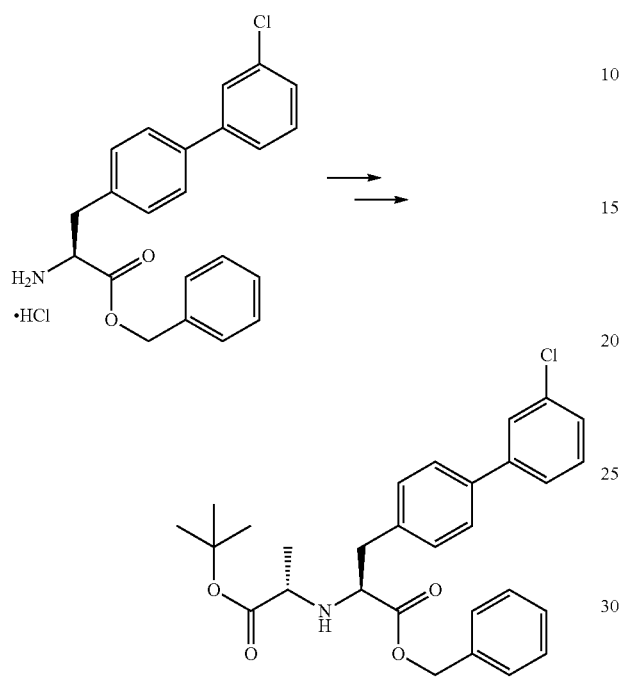

Intermediate 12-2 was prepared using similar procedure as intermediate 1 and intermediate 2 with appropriate reagent. MS: m/z (MH+) 494; HPLC retention time 1.50 min (HPLC condition C).

It can be seen that the compounds of the invention are useful as inhibitors of Neutral endopeptidase (EC 3.4.24.11) activity and therefore useful in the treatment of diseases and conditions associated with Neutral endopeptidase (EC 3.4.24.11) activity such as the diseases disclosed herein.

It will be understood that the invention has been described by way of example only and modifications may be made whilst remaining within the scope and spirit of the invention.

What is claimed is:

1. The compound of Formula III:

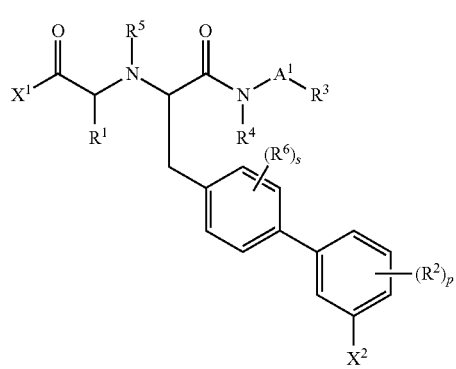

III wherein
$X^1$ represent OH or O-$C_{1-6}$-alkyl;
$A^1$ is a bond or $CH_2$;
$R^1$ is methyl or ethyl;
$R^5$ and $R^4$ are H;
$R^3$ is tetrazole;
$X^2$ is halo;
for each occurrence, $R^2$ is independently $C_{1-6}$-alkoxy, hydroxy, halo, $C_{1-6}$-alkyl, cyano or trifluoromethyl; and
p is 0 or an integer from 1 to 4;
$R^6$ for each occurrence is independently halo, hydroxy, $C_{1-7}$alkoxy, halo, $C_{1-7}$alkyl or halo-$C_{1-7}$alkyl; and
s is 0 or an integer from 1 to 4;
or a pharmaceutically acceptable salt thereof.

2. The compound according to claim 1 of formula IV:

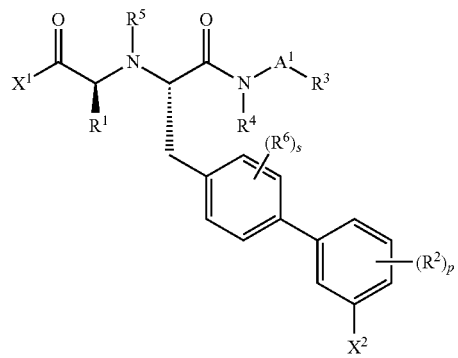

IV or a pharmaceutically acceptable salt thereof.

3. The compound according to claim 1 wherein s is 0; or a pharmaceutically acceptable salt thereof.

4. The compounds according to claim 1 wherein $X^2$ is Cl, or a pharmaceutically acceptable salt thereof.

5. The compound according to claim 1 selected from:
(S)-2-[(S)-2-(3'-chloro-biphenyl-4-yl)-1-(1H-tetrazol-5-ylcarbamoyl)-ethylamino]-propionic acid ethyl ester;
(S)-2-[(S)-2-(3'-chloro-biphenyl-4-yl)-1-(1H-tetrazol-5-ylcarbamoyl)-ethylamino]-propionic acid; and
or a pharmaceutically acceptable salt thereof.

6. A pharmaceutical composition comprising a compound according to claim 1 or a pharmaceutically acceptable salt thereof and one or more pharmaceutically acceptable carriers.

7. A pharmaceutical composition comprising a compound according to claim 5 or a pharmaceutically acceptable salt thereof and one or more pharmaceutically acceptable carriers.

8. A combination comprising: a compound according to claim 1, or a pharmaceutically acceptable salt thereof and one or more therapeutically active agents selected from HMG-Co-A reductase inhibitor, an anigiotensin receptor blocker, angiotensin converting enzyme Inhibitor, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors, a CETP inhibitor and a phophodiesterase type 5 (PDE5) inhibitor.

9. A combination comprising: a compound according to claim 5 or a pharmaceutically acceptable salt thereof and one or more therapeutically active agents selected from HMG-Co-A reductase inhibitor, an anigiotensin receptor blocker, angiotensin converting enzyme Inhibitor, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors, a CETP inhibitor and a phophodiesterase type 5 (PDE5) inhibitor.

10. A method of treating a disorder or a disease associated with neutral endopeptidase EC. 3.4. 24.11. activity in a subject in need thereof, comprising: administering to the subject a therapeutically effective amount of the compound according to claim 1 or a pharmaceutically acceptable salt thereof; wherein the disorder or the disease is selected from hypertension, resistant hypertension, pulmonary hypertension, pulmonary arterial hypertension, isolated systolic hypertension, peripheral vascular disease, and congestive heart failure.

11. A method of treating a disorder or a disease associated with neutral endopeptidase EC. 3.4. 24.11. activity in a subject in need thereof, comprising: administering to the subject a therapeutically effective amount of the compound according to claim 5 or a pharmaceutically acceptable salt thereof; wherein the disorder or the disease is selected from hypertension, resistant hypertension, pulmonary hypertension, pulmonary arterial hypertension, isolated systolic hypertension, peripheral vascular disease, and congestive heart failure.

\* \* \* \* \*